United States Patent
Laby et al.

(10) Patent No.: US 11,420,021 B2
(45) Date of Patent: Aug. 23, 2022

(54) FLUID-ACTUATED DISPLACEMENT FOR CATHETERS, CONTINUUM MANIPULATORS, AND OTHER USES

(71) Applicant: Project Moray, Inc., Belmont, CA (US)

(72) Inventors: Keith Phillip Laby, Oakland, CA (US); Mark D. Barrish, Belmont, CA (US)

(73) Assignee: Project Moray, Inc., Belmont, CA (US)

( * ) Notice: Subject to any disclaimer, the term of this patent is extended or adjusted under 35 U.S.C. 154(b) by 363 days.

(21) Appl. No.: 16/676,921

(22) Filed: Nov. 7, 2019

(65) Prior Publication Data

US 2020/0069917 A1  Mar. 5, 2020

Related U.S. Application Data

(63) Continuation of application No. PCT/US2019/013942, filed on Jan. 17, 2019, and a
(Continued)

(51) Int. Cl.
*A61M 25/01* (2006.01)
*A61M 25/10* (2013.01)
(Continued)

(52) U.S. Cl.
CPC ....... *A61M 25/0155* (2013.01); *A61F 2/2433* (2013.01); *A61F 2/2436* (2013.01);
(Continued)

(58) Field of Classification Search
CPC .......... A61F 2/2427–2439; A61F 2/243–2433; A61F 2/2436; A61F 2/958–2002/9586; A61F 2/962–2002/9665; A61F 2/011
See application file for complete search history.

(56) References Cited

U.S. PATENT DOCUMENTS 3,284,964 A   11/1966 Saito
3,459,221 A   8/1969 Axelrod
(Continued)

FOREIGN PATENT DOCUMENTS

| WO | 2007053625 A1 | 5/2007 |
|----|---------------|--------|
| WO | 2012019156 A1 | 2/2012 |
| WO | 2014128507 A2 | 8/2014 |
| WO | 2019043775 A1 | 7/2019 |

OTHER PUBLICATIONS

"3-D Printing of Electrically Conductive Materials Literature Review", Appropedia: The sustainability Wiki, By Michigan Tech's Open Sustainability Technology Lab, Accessed from Internet on: Jul. 13, 2016, 9 pages.
(Continued)

*Primary Examiner* — Diane D Yabut
*Assistant Examiner* — Brigid K Byrd
(74) *Attorney, Agent, or Firm* — Kilpatrick Townsend & Stockton LLP

(57) ABSTRACT

Catheter-supported therapeutic and diagnostic tools can be introduced into a patient body with a sheath slidably disposed over the tool. Once the tool is aligned with a target tissue, a first fluid-driven actuator can move the sheath axially from over the tool, for example, to allow a stent, stent-graft, prosthetic valve, or other self-expanding tool, to expand radially within the cardiovascular system, without having to transmit large deployment forces along the catheter shaft and sheath from outside the patient. A second fluid-driven actuator can be arranged in opposition to the first actuator to control release of the expanding tool or to recapture the tool within the sheath. The first and/or second actuators may comprise a balloon having a diameter larger than the sheath to provide the desired deployment and recapture forces with moderate fluid pressure.

20 Claims, 18 Drawing Sheets

Related U.S. Application Data continuation-in-part of application No. 15/469,085, filed on Mar. 24, 2017, now Pat. No. 10,512,757.

(60) Provisional application No. 62/618,551, filed on Jan. 17, 2018, provisional application No. 62/313,390, filed on Mar. 25, 2016.

(51) Int. Cl.
*A61F 2/24* (2006.01)
*A61M 25/00* (2006.01)

(52) U.S. Cl.
CPC .. *A61M 25/0122* (2013.01); *A61M 25/10181* (2013.11); *A61M 25/10184* (2013.11); *A61M 2025/0024* (2013.01); *A61M 2025/0058* (2013.01); *A61M 2025/1068* (2013.01)

(56) References Cited

U.S. PATENT DOCUMENTS

| | | | |
|---|---|---|---|
| 3,523,547 A | 8/1970 | Hatch, Jr. et al. | |
| 3,915,194 A | 10/1975 | Friedrich | |
| 3,934,605 A | 1/1976 | Legris | |
| 4,082,324 A | 4/1978 | Obrecht | |
| 4,230,143 A | 10/1980 | Dettmann et al. | |
| 4,494,417 A | 1/1985 | Larson et al. | |
| 4,762,130 A | 8/1988 | Fogarty et al. | |
| 4,784,042 A | 11/1988 | Paynter | |
| 4,794,912 A | 1/1989 | Lia | |
| 4,838,859 A | 6/1989 | Strassmann | |
| 4,875,897 A | 10/1989 | Lee | |
| 4,890,611 A | 1/1990 | Monfort et al. | |
| 4,893,613 A | 1/1990 | Hake | |
| 4,900,218 A | 2/1990 | Sutherland | |
| 4,983,165 A | 1/1991 | Loiterman | |
| 5,018,506 A | 5/1991 | Danna et al. | |
| 5,304,132 A | 4/1994 | Jang | |
| 5,308,356 A | 5/1994 | Blackshear, Jr. et al. | |
| 5,337,733 A | 8/1994 | Bauerfeind et al. | |
| 5,413,107 A | 5/1995 | Oakley et al. | |
| 5,469,756 A | 11/1995 | Feiten | |
| 5,476,100 A | 12/1995 | Galel | |
| 5,489,270 A | 2/1996 | van Erp | |
| 5,501,667 A | 3/1996 | Verduin, Jr. | |
| 5,529,088 A | 6/1996 | Asou | |
| 5,534,007 A | 7/1996 | St. Germain et al. | |
| 5,545,209 A * | 8/1996 | Roberts ............... | A61F 2/958 604/103.05 |
| 5,619,993 A | 4/1997 | Lee | |
| 5,817,101 A * | 10/1998 | Fiedler ................. | A61F 2/95 623/1.11 |
| 5,820,595 A | 10/1998 | Parodi | |
| 5,823,955 A | 10/1998 | Kuck et al. | |
| 5,865,801 A | 2/1999 | Houser | |
| 6,066,125 A | 5/2000 | Webster, Jr. | |
| 6,113,608 A | 9/2000 | Monroe et al. | |
| 6,146,339 A | 11/2000 | Biagtan et al. | |
| 6,178,872 B1 | 1/2001 | Schulz | |
| 6,503,194 B2 | 1/2003 | Pauker | |
| 6,527,739 B1 | 3/2003 | Bigus et al. | |
| 6,648,879 B2 | 11/2003 | Joye et al. | |
| 6,811,550 B2 | 11/2004 | Holland et al. | |
| 6,827,731 B2 | 12/2004 | Armstrong et al. | |
| 6,875,170 B2 | 4/2005 | Francois et al. | |
| 6,928,313 B2 | 8/2005 | Peterson | |
| 6,951,226 B2 | 10/2005 | Eriksson et al. | |
| 7,060,062 B2 | 6/2006 | Joye et al. | |
| 7,373,955 B2 | 5/2008 | Steinberg | |
| 7,422,579 B2 | 9/2008 | Wahr et al. | |
| 7,570,981 B2 | 8/2009 | Peterson | |
| 7,578,787 B2 | 8/2009 | Boese et al. | |
| 7,780,723 B2 | 8/2010 | Taylor | |
| 7,824,391 B2 | 11/2010 | Gesswein | |
| 7,850,683 B2 | 12/2010 | Elkins et al. | |
| 7,879,004 B2 | 2/2011 | Seibel et al. | |
| 7,957,790 B2 | 6/2011 | Kleen | |
| 7,963,911 B2 | 6/2011 | Turliuc | |
| 8,125,755 B2 | 2/2012 | Garcia et al. | |
| 8,201,473 B2 | 6/2012 | Knoll | |
| 8,372,055 B2 | 2/2013 | Thornton et al. | |
| 8,388,520 B2 | 3/2013 | Stefanchik et al. | |
| 8,398,540 B2 | 3/2013 | Hassidov et al. | |
| 8,423,115 B2 | 4/2013 | Koblish | |
| 8,469,059 B1 | 6/2013 | Forst | |
| 8,764,725 B2 | 7/2014 | Averbuch | |
| 8,845,523 B2 | 9/2014 | Lawrence et al. | |
| 8,863,608 B2 | 10/2014 | Fischer et al. | |
| 10,512,757 B2 | 12/2019 | Laby et al. | |
| 2001/0007070 A1 | 7/2001 | Stewart et al. | |
| 2002/0045929 A1 | 4/2002 | Diaz | |
| 2002/0049408 A1 | 4/2002 | Van Moorlegem et al. | |
| 2002/0058951 A1 | 5/2002 | Fiedler | |
| 2003/0069475 A1 | 4/2003 | Banik et al. | |
| 2005/0187467 A1 | 8/2005 | Kleen | |
| 2006/0030923 A1 | 2/2006 | Gunderson | |
| 2006/0058598 A1 | 3/2006 | Esposito | |
| 2006/0074372 A1 | 4/2006 | Haga et al. | |
| 2006/0084964 A1 | 4/2006 | Knudson et al. | |
| 2006/0129142 A1 | 6/2006 | Reynolds | |
| 2006/0235368 A1 | 10/2006 | Oz | |
| 2007/0060997 A1 | 3/2007 | de Boer | |
| 2007/0100235 A1 | 5/2007 | Kennedy, II | |
| 2007/0123925 A1 | 5/2007 | Benjamin et al. | |
| 2007/0169761 A1 | 7/2007 | Price | |
| 2007/0270686 A1 | 11/2007 | Ritter et al. | |
| 2007/0288095 A1 | 12/2007 | Wirtel et al. | |
| 2008/0091073 A1 | 4/2008 | Park | |
| 2008/0215008 A1 | 9/2008 | Nance et al. | |
| 2009/0076584 A1 | 3/2009 | Mao et al. | |
| 2009/0105816 A1 | 4/2009 | Olsen et al. | |
| 2009/0281523 A1 | 11/2009 | Sacco et al. | |
| 2010/0168665 A1 | 7/2010 | Skerven | |
| 2011/0112632 A1 | 5/2011 | Chau et al. | |
| 2011/0270126 A1 | 11/2011 | Gunday et al. | |
| 2011/0295247 A1 | 12/2011 | Schlesinger et al. | |
| 2011/0295248 A1 | 12/2011 | Wallace et al. | |
| 2012/0271319 A1 | 10/2012 | Bromander et al. | |
| 2012/0310227 A1 | 12/2012 | Katou | |
| 2013/0091974 A1 | 4/2013 | Riwan et al. | |
| 2013/0096377 A1 | 4/2013 | Duindam et al. | |
| 2013/0103019 A1 | 4/2013 | Joye et al. | |
| 2013/0178838 A1 | 7/2013 | Malkowski | |
| 2013/0231735 A1 * | 9/2013 | Deem ................. | A61F 2/95 623/2.11 |
| 2013/0296983 A1 | 11/2013 | Keller et al. | |
| 2013/0304181 A1 | 11/2013 | Green et al. | |
| 2014/0046250 A1 | 2/2014 | Jain et al. | |
| 2014/0062405 A1 | 3/2014 | Videbaek | |
| 2014/0142666 A1 | 5/2014 | Phelan et al. | |
| 2014/0200649 A1 | 7/2014 | Essinger et al. | |
| 2014/0243688 A1 | 8/2014 | Caron et al. | |
| 2014/0276933 A1 | 9/2014 | Hart et al. | |
| 2014/0276934 A1 | 9/2014 | Balaji et al. | |
| 2015/0057738 A1 * | 2/2015 | Hepke ................. | A61F 2/2436 623/1.11 |
| 2015/0209558 A1 | 7/2015 | Charlebois et al. | |
| 2015/0265807 A1 | 9/2015 | Park et al. | |
| 2016/0128767 A1 | 5/2016 | Azamian et al. | |
| 2016/0279388 A1 | 9/2016 | Barrish et al. | |
| 2017/0021132 A1 | 1/2017 | Laby et al. | |
| 2017/0021143 A1 | 1/2017 | Barrish et al. | |
| 2017/0157361 A1 | 6/2017 | Barrish et al. | |
| 2017/0157363 A1 | 6/2017 | Barrish et al. | |
| 2018/0071492 A1 | 3/2018 | Laby et al. | |
| 2018/0085559 A1 | 3/2018 | Laby et al. | |
| 2018/0185148 A1 | 7/2018 | Hariton et al. | |
| 2018/0200483 A1 | 7/2018 | Laby et al. | |

OTHER PUBLICATIONS

"A Tiny Spectrometer that Costs 10 Bucks", Omed Qualified Suppliers, Available online at: http://www.qmed.com/mpmn/

(56) References Cited

OTHER PUBLICATIONS medtechpulse/tiny-spectrometer-costs-10-buckscid=nl.qmed02. 20141216, Dec. 12, 2014, 3 pages.
"Accelerometer, Gyro and IMU Buying Guide", Sparkfun, Available online at https://www.sparkfun.com/pages/accel_gyro_guide, Accessed from the internet on Jul. 14, 2016, 10 pages.
"Balloons and Balloon Catheters fromTeleflexMedical OEM", Teleflex Incorporated, Available online at http://www.teleflexmedicaloem.com/diagnostic-and-interventional-catheters/balloon-catheters/, Accessed from Internet on: Jul. 13, 2016, 3 pages.
"Compliant Robots", EUCog Wiki, Available online at http://www.eucognition.org/eucog-wiki/Compliant_robots, Accessed from Internet on: Aug. 11, 2016, 5 pages.
"Convoluted Tubing to an Outer Diameter of 65 mm", ProfilePipe Machinery Inc., Available online at http://www.profilepipe.com/small_corrugators.html, Accessed from Internet on: Jul. 14, 2016, 2 pages.
"CoreValve™ System", Medtronic, Transcatheter Aortic Valve Delivery Catheter System Compression Loading System, 2014, 61 pages.
"Corrugator Technologies: Overview and New Developments", Plastics, Corrugator technologies overview, Available at http://www.plastics.gl/extrusion-profile/corrugator-technologies-overview/, Accessed from Internet on: Jul. 14, 2016, 8 pages.
"Corrugators and Pulsating Corrugators", Corma Inc., Available online at http://corma.com/products/corrugators-pulsating-corrugators/, Accessed from Internet on: Jul. 14, 2016, 3 pages.
"Deflectable and Steerable Catheter Handbook", Creganna Tactx Medical, Terminology Guide & Design Options, Available online at http://www.creganna.com/wp-content/uploads/Steeringand-DeflectionTerminologyrev3.pdf, 7 pages.
"Edwards Tightens Transcatheter Valve Stranglehold", EP Vantage, Available online at http://www.epvantage.com/Universal/View.aspxtype=Story&id=580885&isEPVantage=yes, Jun. 18, 2015, 2 pages.
"How 3-D Printing Can Help Accelerate Fluidic Manifold Delivery", Omed Qualified Suppliers, Available online at http://www.qmed.com/mpmn/medtechpulse/how-3-d-printing-can-help-accelerate-fluidic-manifold-deliverycid=nl.qmed02.20150507, May 6, 2015, 3 pages.
"How Micro-Location Could Boost Healthcare IoT", Qmed, Electronic Components, Available online at http://www.qmed.com/mpmn/medtechpulse/how-micro-location-could-boost-healthcare-iotcid=nl.x.qmed02.edt.aud.qmed.20160606, Jun. 3, 2016, 2 pages.
"Introducing 3-D Injection Molding", Omed Qualified Suppliers, Qmed, Available online at http://www.qmed.com/mpmn/gallery/image/4-introducing-3-d-injection-molding, Accessed from Internet on: Nov. 7, 2014, 2 pages.
"LabSmith uProcess™ System", LabSmith, Inc., Microfluidic Automation, Available online at http://www.labsmith.com/products/LabSmith_uProcess_Brochure.pdf_ga=1.142274551.472763250.1458083262., 2015, 6 pages.
"Microfluidics and Microfluidic Devices: A Review", Elveflow Plug & Play, Available online at http://www.elveflow.com/microfluidic-tutorials/microfluidic-reviews-and-tutorials/microfluidics-and-microfluidic-device-a-review/, 2015, 10 pages.
"Nanotube Yarns Twist Like Muscles", BBC News Science & Environment, Available online at http://www.bbc.co.uk/news/science-environment-15287185, Oct. 14, 2011, 8 pages.
"Overcoming Engineering Challenges: Developing a Tiny Robotically Steerable Guidewire", Qmed Qualified Suppliers, Medtech Pulse Blog, Available online at http://www.qmed.com/mpmn/medtechpulse/overcoming-engineering-challenges-developing-tiny-robotically-steerable-guidewirecid=nl_qmed_daily, Feb. 15, 2013, 2 pages.
"Peripheral Dilatation Catheter Peripheral Dilatation System", Nucryovascular, LLC, Vascular solutions, PolarCath™ over-the-wire, Available online at www.vasc.com, Jun. 2015, pp. 1-12.
"PTA Sphere-Curve", Tokai Medical Products Inc. Available online at: http://www.tokaimedpro.co.jp/en/products/2009/000056.html, Accessed from Internet on: Jul. 14, 2016, 2 pages.
"Researchers Compare Two-Year Clinical Outcomes of Mitral Valve Replacement and Repair in Treating Severe Valve Regurgitation", IMount Sinai Hospital, Available online at http://www.mountsinai.org/about-us/newsroom/press-releases/researchers-compare-twoyear-clinical-outcomes-of-mitral-valve-replacement-and-repair-, Nov. 9, 2015, 2 pages.
"Scientific Tubing", PEELSIL™ Tubing, SGE, Glass Lined Tubing (GLT™), Available online atwww.sge.com, Fused Silica Tubing brochure PD-0230-Aw, 2001, 6 pages.
"Systematic Expertise Through Continuous Further Development", Festo, Bionic Handling Assistant, Available online at https://www.festo.com/net/supportportal/files/42050/brosch_fc_bha_3_0_en_lo.pdf, Apr. 2012, 6 pages.
"The Benefits of Using Bend Sensors", Flexpoint Sensor Systems, Inc., Sensor Products Inc., Available online at www.sensorprod.com, Jul. 2016, 2 pages.
"The Effect of Extrusion and Blow Molding Parameters on Angioplasty Balloon Production", MDDI, Medical Plastics, Available online at http://www.mddionline.com/article/effect-extrusion-and-blow-molding-parameters-angioplasty-balloon-production, May 1, 1998, 4 pages.
"Tiny Artificial Muscles", Qmed Qualified Suppliers, Available online at http://www.qmed.com/mpmn/gallery/image/1-tiny-artificial-muscles, Accessed from Internet on: Jul. 14, 2016, 1 page.
"Tubing, Stainless Steel Tubing and Terry-Tool Tubing Cutter", SGE Analytical Science, 2011, 10 pages.
"U.S. Aortic Stenosis Disease Prevalence and Treatment Statistics", John Muir Health, Facts and Figures, Available Online at https://www.johnmuirhealth.com/services/cardiovascular-services/intervention/transcatheter-aortic-valve-replacement/facts-and-figures.html, Accessed from Internet on: Jul. 14, 2016, 3 pages.
Arsalan et al., "Comparison of Current Costs and Reimbursement for Transcatheter and Surgical Aortic Valve Replacement", J. Am. Coll. Cardiol., vol. 67, No. 13, ACC.I2 Interventional Cardiology, Available online at http://content.onlinejacc.org/article.aspxarticleid=2508037, Apr. 5, 2016, 2 pages.
Atzori et al., "Indoor Navigation System Using Image and Sensor Data Processing on a Smartphone", Optimization of Electrical and Electronic Equipment (OPTIM), 2012 13th International Conference, Available online at https://www.researchgate.net/publication/261267019_Indoor_navigation_system_using_image_and_sensor_data_processing_on_a_smartphone, May 24-26, 2012, pp. 1158-1163.
Au et al., "Microvalves and Micropumps forBioMEMS", Micromachines, vol. 2, ISSN 2072-666X, Available online at www.mdpi.com/journal/micromachines, 2011, pp. 179-220.
Backer et al., "Percutaneous Transcatheter Mitral Valve Replacement", Circulation: Cardiovascular Interventions, Available online at http://circinterventions.ahajournals.org/content/7/3/400.full, Jun. 2014, pp. 400-409.
Bar-Cohen, "Worldwide ElectroActive Polymers", EAP (Artificial Muscles) Newsletter, vol. 16, No. 1, (The 31th issue), Available online at http://eap.jpl.nasa.gov, Jun. 2014, pp. 1-18.
Beahm et al., "Catheter Bonding Technology Overview", Avaialble online at www.beahmdesigns.com, Apr. 2012, 4 pages.
Biswal et al., "Development of an Active Catheter Mechanism Using IPMC for in Vivo Inspection", Journal of Mechatronics and Automation vol. 1, No. 1, Available online at: http://www.academia.edu/10757534/Development_of_an_Active_Catheter_Mechanism_using_IPMC_for_in_vivo_Inspection, 2014, pp. 1-10.
Bolling, "Can We Predict Mitral Valve Repair Rates by Individual Surgeons' Mitral Volume?", Tex Heart Inst J., vol. 38, No. 6, 8th Current Trends in Aortic and Cardiothoracic Surgery, Available online at http://www.ncbi.nlm.nih.gov/pmc/articles/PMC3233323/, 2011, pp. 703-704.
Buntz, "Forget IoT: The Internet of Moving Things Is Where It Is at", Qmed, Available online at http://www.qmed.com/mpmn/medtechpulse/forget-iot-internet-moving-things-where-it, Dec. 10, 2014, 3 pages.
Buntz, "Graphene Breakthrough Could Be a Boon to Flexible Electronics", Electronic Components, Qmed, Available online at

(56) References Cited

OTHER PUBLICATIONS http://www.qmed.com/mpmn/medtechpulse/graphene-breakthrough-could-be-boon-flexible-electronicscid=nl.qmed02, Nov. 14, 2013, 1 page.
Buntz, "How Tiny Artificial Muscles Could Be Huge Energy Savers", Motion Control, Qmed, Available online at http://www.qmed.com/mpmn/medtechpulse/how-tiny-artificial-muscles-could-be-huge-energy-saverscid=nl.qmed02.20150223, Feb. 20, 2015, 3 pages.
Buntz, "Using a T-Shirt Printer to Make Medical Circuits", Qmed, Electronic Components, Available online at http://www.qmed.com/mpmn/medtechpulse/using-t-shirt-printer-make-medical-circuits, Nov. 17, 2014, 3 pages.
Catherine et al., "Comparative Review of Endoscopic Devices Articulations Technologies Developed for Minimally Invasive Medical Procedures", Applied Bionics and Biomechanics, vol. 8, No. 2, 2011, pp. 151-171.
Chakraborty et al., "Mems Micro-Valve for Space Applications", Sensors and Actuators A: Physical, vol. 83, Nos. 1-3, 2000, pp. 188-193.
Chandgadkar, "An Indoor Navigation System For Smartphones", Available online at http://www.doc.ic.ac.uk/teaching/distinguished-projects/2013/a.chandgadkar.pdf, Jun. 18, 2013, 80 pages.
Chang et al., "Electrostatically-Actuated Reconfigurable Elastomer Microfluidics", Available online at http://people.eecs.berkeley.edu/~maharbiz/HH_paper_mpchang_0008.pdf, 2008, 4 pages.
Chen et al., "High-Pressure On-Chip Mechanical Valves for Thermoplastic Microfluidic Devices", Lab on a Chip, vol. 9, Oct. 6, 2009, pp. 3511-3516.
Clippard New!, "New! 7 mm Electronic Valves", Available online at http://www.clippard.com/products/electronic-valve-7mm, Accessed from internet on Jul. 13, 2016, 2 pages.
Conrad et al., "Closed Loop Task Space Control of an Interleaved Continuum-Rigid Manipulator", IEEE International Conference on Robotics and Automation, Available online at http://robotics.engr.wisc.edu/cgi-bin/wikiwp/category/continuum-robotics/, May 26-30, 2015, 8 pages.
Coyne, "Comprehensive Manufacturing of Microfluidic Diagnostic Devices", IVD, MDDI Medical Device and Diagnostic Industry, Jun. 17, 2014, 4 pages.
Dabove et al., "Inertial Sensors for Smartphones Navigation", SpringerPlus, vol. 4, No. 834, Available online at http://www.ncbi.nlm.nih.gov/pmc/articles/PMC4695469/, Dec. 30, 2015, pp. 1-18.
D'Arcy et al., "Valvular Heart Disease: The Next Cardiac Epidemic", vol. 97, No. 2, Available online at http://heart.bmj.com/content/97/2/91.extract, 2011, 2 pages.
De Sars et al., "A Practical Approach to the Design and Control of Active Endoscopes", Mechatronics, vol. 20, No. 2, Available online at: http://www.elsevierscitech.com/pdfs/Mechatronics_DeSars.pdf, Mar. 2010, pp. 251-264.
DMQ Inc., "Product Datasheet: silQflo™ Silicon Servo Valve", Available online at http://www.dmq-us.com/wp-content/uploads/2015/02/SSV-Datasheet-Rev-1.001.pdf, Apr. 2015, 2 pages.
Don et al., "Novel Velocity Model to Improve Indoor Localization Using Inertial Navigation With Sensors on a Smart Phone", Avaialble online at http://arxiv.org/pdf/1601.03004.pdf, Jan. 12, 2016, 5 pages.
Dupont et al., "Snakes, Worms and Catheters: Continuum and Serpentine Robots for Minimally Invasive Surgery", IEEE ICRA Full Day Workshop, May 3, 2010, 60 pages.
Eitel, "The Rise of Soft Robots and the Actuators that Drive Them", Available online at http://machinedesign.com/robotics/rise-soft-robots-and-actuators-drive-them, Sep. 12, 2013, 7 pages.
Fedak et al., "Evolving Concepts and Technologies in Mitral Valve Repair", Circulation, vol. 117, No. 7, Available online at http://circ.ahajournals.org/content/117/7/963.full, Feb. 19, 2008, pp. 963-974.
Fite et al., "A Gas-Actuated Anthropomorphic Prosthesis forTranshumeral Amputees", IEEE Transactions on Robotics, vol. 24, No. 1, Feb. 2008, pp. 159-169.
Fornell, "Transcatheter Mitral Valve Replacement Devices in Development", Diagnostic and Interventional Cardiology, Available online at http://www.dicardiology.com/article/transcatheter-mitral-valve-replacement-devices-development, Dec. 30, 2014, 5 pages.
Fu et al., "Research on the Axis Shape of an Active Catheter", Int. J. Med. Robot.; vol. 4, No. 1, Mar. 2008, pp. 69-76.
Fu et al., "Steerable Catheters in Minimally Invasive Vascular Surgery", Int. J. Med. Robot., vol. 5, No. 4, Dec. 2009, pp. 381-391.
Gionata et al., "An Inertial and Qr Code Landmarks-Based Navigation System for Impaired Wheelchair Users", Ambient Assisted Living, May 29, 2014, pp. 1-10.
Grube, "Development of a TMVR Device Challenge to Innovators", ICI meeting, Dec. 13-15, 2015, 30 pages.
Haga et al., "Active Bending Catheter and Endoscope Using Shape Memory Alloy Actuators", Shape Memory Alloys, Available online at: www.intechopen.com, Oct. 18, 2010, pp. 107-126.
Haga et al., "Multi-Functional Active Catheter", Available online at http://bdml.stanford.edu/twiki/pub/Haptics/DesignReferencesSummer2009/MultifunctionalActiveCatheter.pdf, Nov. 2000, pp. 147-186.
Herrmann et al., "Novel Transcatheter Approaches", Heart Valve Summit, American association of Thoracic surgery, Available online at http://aats.org/multimedia/files/valve/2015/Presentations/Thursday/600-Herrmann.pdf, 2015, 26 pages.
Ikeuchi et al., "Development of Pressure-Driven Micro Active Catheter using Membrane Micro Emboss Following Excimer Laser Ablation (MeME-X) Process", IEEE International Conference on Robotics and Automation, Available online at http://ir.nul.nagoya-u.ac.jP/jspui/bitstream/2237/13924/1/ICRA09_MeMEX.pdf, May 12-17, 2009, pp. 4469-4472.
Jagadeesan, "Design and Control of an Active Catheter", Available online at http://scholar.harvard.edu/jayender/activecatheter, Accessed from Internet on: Jul. 14, 2016, 2 pages.
Jia et al., "Online Camera-Gyroscope Auto-Calibration for Cellphones", IEEE Transactions on Image Processing, Available online at http://users.ece.utexas.edu/~bevans/papers/2015/autocalibration/autocalibrationIEEETransImageProcPaperDraft.pdf, 2013, 11 pages.
Johnson, "Modeling of Frictional Gas Flow in a Piezoelectrically Actuated High-Pressure Microvalve for Flowrate Control", IAI Auburn University, Electronic Theses and Dissertations, Dec. 16, 2005, 197 pages.
Jung et al., "A Modeling Approach for Continuum Robotic Manipulators: Effects of Nonlinear Internal Device Friction", IEEE/RSJ International Conference on Intelligent Robots and Systems, Sep. 25-30, 2011, pp. 5139-5146.
Kasahara et al., "Surface Modification of Polyethylene Terephthalate (PET) by 172-nm Excimer lamp", Electronic Theses and Dissertations, vol. 5, No. 1, 2012, pp. 47-54.
Kato et al., "An Inchworm Type In-Pipe Mobile Microrobot Driven by Three Gas-Liquid Phase-Change Actuators", Proceedings of the Annual Meeting—American Society for Precision Engineering, 2003, 4 pages.
Kim et al., "Materials for Multifunctional Balloon Catheters with Capabilities in Cardiac Electrophysiological Mapping and Ablation Therapy", Nat Mater., vol. 10, No. 4, Apr. 2011, pp. 316-323.
Kirby et al., "Microfluidic Routing of Aqueous and Organic Flows at High Pressures: Fabrication and Characterization of Integrated Polymer Microvalve Elements", Lab on a Chip, vol. 5, Feb. 2005, pp. 184-190.
Korane, "Robot Imitates an Elephant's Trunk", Available online at http://machinedesign.com/robotics/robot-imitates-elephant-s-trunk, Sep. 13, 2010, 5 pages.
Langelaar et al., "Modeling of a Shape Memory Alloy Active Catheter", 45th AIAA/ASME/ASCE/AHS/ASC Structures, Structural Dynamics & Materials Conference, Apr. 19-22, 2004, 16 pages.
Lee et al., "Fabrication, Characterization, and Computational Modeling of a Piezoelectrically Actuated Microvalve for Liquid Flow Control", Journal of Microelectromechanical Systems, vol. 15, No. 3, IEEE, Jun. 2006, pp. 686-696.
Levy, "Tiny Ultrasound Camera Images Blood Vessel Interior in 3-D", Medical Imaging, Qmed, Available online at http://www.qmed.com/mpmn/medtechpulse/tiny-ultrasound-camera-images-blood-vessel-interior-3-dcidnl.qmed02, Mar. 3, 2014, 5 pages.

(56) References Cited

OTHER PUBLICATIONS

Maglione et al., "Ultra-High-Pressure Balloon Angioplasty for Treatment of Resistant Stenoses Within or Adjacent to Previously Implanted Pulmonary Arterial Stents", Circulation: Cardiovascular Interventions, Available online at http://circinterventions.ahajournals.org/content/2/1/52.full, Feb. 2009, pp. 52-58.

Malek et al., "Femtosecond Laser Machining and Lamination for Large-Area Flexible Organic Microfluidic Chips", The European Physical Journal Applied Physics, vol. 46, No. 1, Apr. 2009, 8 pages.

Mazzarese, "Low-Profile Balloon Catheters are Critical to TAVR's Success", Medical Tubing Types by MDDI Staff, Available online at http://www.mddionline.com/article/low-profile-balloon-catheters-are-critical-tavr-success-10-21-2014cid=nl.mddi01.20141023, Oct. 21, 2014, 3 pages.

Messenger, "A Comprehensive Guide to the U.S. TAVR Market: Surveying the Field", Med Device Online, Available online at: http://www.meddeviceonline.com/doc/a-comprehensive-guide-to-the-u-s-tavr-market-surveying-the-field-0001, Apr. 12, 2016, 7 pages.

Mohty et al., "Valvular Heart Disease in Elderly Adults", UpToDate, Available online at http://www.uptodate.com/contents/valvular-heart-disease-in-elderly-adults, Accessed from Internet on: Jul. 14, 2016, 6 pages.

Mueller et al., "An Overview of Mems-Based Micropropulsion Developments at JPL", Acta Astronautica, vol. 52, Nos. 9-12, May-Jun. 2003, 15 pages.

Mueller et al., "Design and Fabrication of MEMS-Based Micropropulsion Devices at JPL", Proceedings of SPIE, vol. 4558, Oct. 2001, pp. 57-71.

Muller et al., "Remote Control Catheter Navigation: Options for Guidance Under MRI", Journal of Cardiovascular Magnetic Resonance, vol. 14, No. 1, Jun. 1, 2012, pp. 1-9.

Newmarker, "How Lasers are Changing MedTech", Lasers, Qmed, Available online at http://www.qmed.com/mpmn/medtechpulse/how-lasers-are-changing-medtechcid=nl.qmed02, Jan. 14, 2014, 3 pages.

Newmarker, "How Scotch Tape is Driving Diagnostics Breakthroughs", Medical Plastics, Qmed, Available online at http://www.qmed.com/mpmn/medtechpulse/how-scotch-tape-driving-diagnostics-breakthroughscid=nl.qmed02.20141002, Oct. 1, 2014, 3 pages.

Nolker et al., "Differences in Tissue Injury and Ablation Outcomes in Atrial Fibrillation Patients—Manual versus Robotic Catheters", Journal of Atrial Fibrillation, vol. 6, No. 2, Aug.-Sep. 2013, pp. 82-88.

Oh et al., "A Review of Microvalves", Journal of Micromechanics and Microengineering, vol. 16, Mar. 24, 2006, pp. R13-R39.

Ono et al., "Development of a Cylinder Type Gas-liquid Phase-Change Actuator", 2013, 2 pages.

Parmar, "FDA Approves St. Jude Medical's Force-Sensing Ablation Catheters for AF", Regulatory and Compliance, MDDI Medical Device and Diagnostic Industry, Available online at http://www.mddionline.com/article/fda-approves-st-jude-medicals-force-sensing-ablation-catheters-af-102714cid=nl.mddi01.20141028, Oct. 27, 2014, 3 pages.

Penning et al., "A Combined Modal-Joint Space Control Approach for Minimally Invasive Surgical Continuum Manipulators", Advanced Robotics, vol. 28, No. 16, Jul. 2014, 41 pages.

Penning et al., "An Evaluation of Closed-Loop Control Options for Continuum Manipulators", 2012 IEEE International Conference on Robotics and Automation, May 14-18, 2012, 6 pages.

Penning, "ICRA 2012 Recap", Available online at http://robotics.engr.wisc.edu/cgi-bin/wikiwp/2012/11/icra-2012-recap/, Nov. 11, 2012, 2 pages.

Penning et al., "Towards Closed Loop Control of a Continuum Robotic Manipulator for Medical Applications", IEEE, 2011, 6 pages.

Pollock, "Bionic Ants Could be Tomorrow's Factory Workers", Available online at http://www.reuters.com/article/2015/03/30/us-germany-bionic-ants-idUSKBN0MQ1WD20150330, Mar. 30, 2015, 3 pages.

Preston-Maher et al., "A Technical Review of Minimally Invasive Mitral Valve Replacements", Cardiovascular Engineering and Technology, vol. 6, No. 2, Jun. 2015, pp. 174-184.

Quero et al., "A Novel Pressure Balanced Microfluidic Valve", Proc. Iscas, IEEE, May 26-29, 2002, pp. 1-4.

Rich et al., "Costs for Mitral Valve Surgery According to STS Preoperative Risk: Implications for Transcatheter Mitral Therapies", American Association for Thoracic Surgery, Available Online at http://aats.org/mitral/abstracts/2015/P165.cgi, Apr. 27-28, 2017, 2 pages.

Roriz et al., "Fiber Optic Intensity-Modulated Sensors: A Review in Biomechanics", Photonic Sensors, vol. 2, No. 4, 2012, pp. 315-330.

Rossiter et al., "Printing 3D Dielectric Elastomer Actuators for Soft Robotics", SPIE Proceedings, vol. 7287, Apr. 6, 2009, 2 pages.

Schut, "Corrugator Vacuum Forming", Plastics Technology, Available online at http://www.ptonline.com/articles/'corrugator-vacuum-forming', Jul. 2005, 4 pages.

Shoa et al., "Conducting Polymer Based Active Catheter for Minimally Invasive Interventions inside Arteries", Conf Proc IEEE Eng Med Biol Soc., 2008, 4 pages.

Strickland, "Inside an MRI, a Non-Metallic Robot Performs Prostate Surgery", IEEE Spectrum, Available online at http://spectrum.ieee.org/automaton/robotics/medical-robots/inside-an-mri-a-nonmetallic-robot-performs-prostate-surgery, Jul. 8, 2015, 3 pages.

Takizawa et al., "Development of a Microfine Active Bending Catheter Equipped with MIF Tactile Sensors", Technical Digest. IEEE International MEMS 99 Conference. Twelfth IEEE International Conference on Micro Electro Mechanical Systems, 1999, 7 pages.

Taramasso et al., "Current Challenges in Interventional Mitral Valve Treatment", J. Thorac. Dis., vol. 7, No. 9, Available online at: http://www.ncbi.nlm.nih.gov/pmc/articles/PMC4598533/, 2015, pp. 1536-1542.

Temiz et al., "Lab-on-a-Chip Devices: How to Close and Plug the Lab", Microelectronic Engineering, vol. 132, Jan. 25, 2015, pp. 156-175.

Tung et al., "Laser-Machined Shape Memory Alloy Actuators for Active Catheters", Mechatronics, IEEE/ASME Transactions on, vol. 12, No. 4, Aug. 2007, pp. 439-446.

Van Oosten et al., "Printed Artificial Cilia from Liquid-Crystal Network Actuators Modularly Driven by Light", Nature Materials, vol. 8, Jun. 28, 2009, pp. 677-682.

Veeramani, "A Transformative Tool for Minimally Invasive Procedures: Design, Modeling and Real-time Control of a Polycrystalline Shape Memory Alloy Actuated Robotic Catheter", University Libraries, Apr. 24, 2009, 198 pages.

Walters, "Gas-Flow Calculations: Don't Choke", Applied Flow Technology, Chemical Engineering, Available online at http://www.aft.com/documents/AFT-CE-Gasflow-Reprint.pdf, Jan. 2000, 8 pages.

Wasserman, "Edwards and Medtronic Turn up TAVR Competition with Positive Study Data", FierceBiotech, Available online at http://www.fiercemedicaldevices.com/story/edwards-and-medtronic-turn-tavr-competition-positive-study-data/2015-03-16, Mar. 16, 2015, 3 pages.

Webb et al., "Transcatheter Aortic Valve Implantation: The Evolution of Prostheses, Delivery Systems and Approaches", Archives of Cardiovascular Disease, vol. 105, No. 3, Mar. 2012, pp. 153-159.

Weber et al., "Side-Selective Atrial Transseptal Laser Puncture", The Journal of Innovations in Cardiac Rhythm Management, vol. 4, Dec. 2013, pp. 1481-1485.

Wirtl et al., "White Paper Piezo Technology in Pneumatic Valves", Festo AG & Co. KG, 2014, pp. 1-9.

Wood, "Early Results for Transcatheter Mitral Valve Replacement Reveal Complications and Challenges for the Long Road Ahead", Available online at http://www.tctmd.com/show.aspxid=133937, Feb. 22, 2016, 1 page.

Wutzler et al., "Robotic Ablation of Atrial Fibrillation", Department of Cardiology, vol. 99, Available online at http://www.jove.com/video/52560/robotic-ablation-of-atrial-fibrillation, May 29, 2015, 14 pages.

Yang et al., "Leak-Tight Piezoelectric Microvalve for High-Pressure Gas Micropropulsion", Journal of Microelectromechanical Systems, vol. 13, No. 5, Oct. 2004, pp. 799-807.

(56) References Cited

OTHER PUBLICATIONS

Yarbasi et al., "On the Design of a Continuum Robot with Extendable Balloons", Department of Mechanical Engineering, 2015, 1 page.
You et al., "A Doubly Cross-Linked Nano-Adhesive for the Reliable Sealing of Flexible Microfluidic Devices", Lab Chip., vol. 13, No. 7, Apr. 7, 2013, pp. 1266-1272.

* cited by examiner

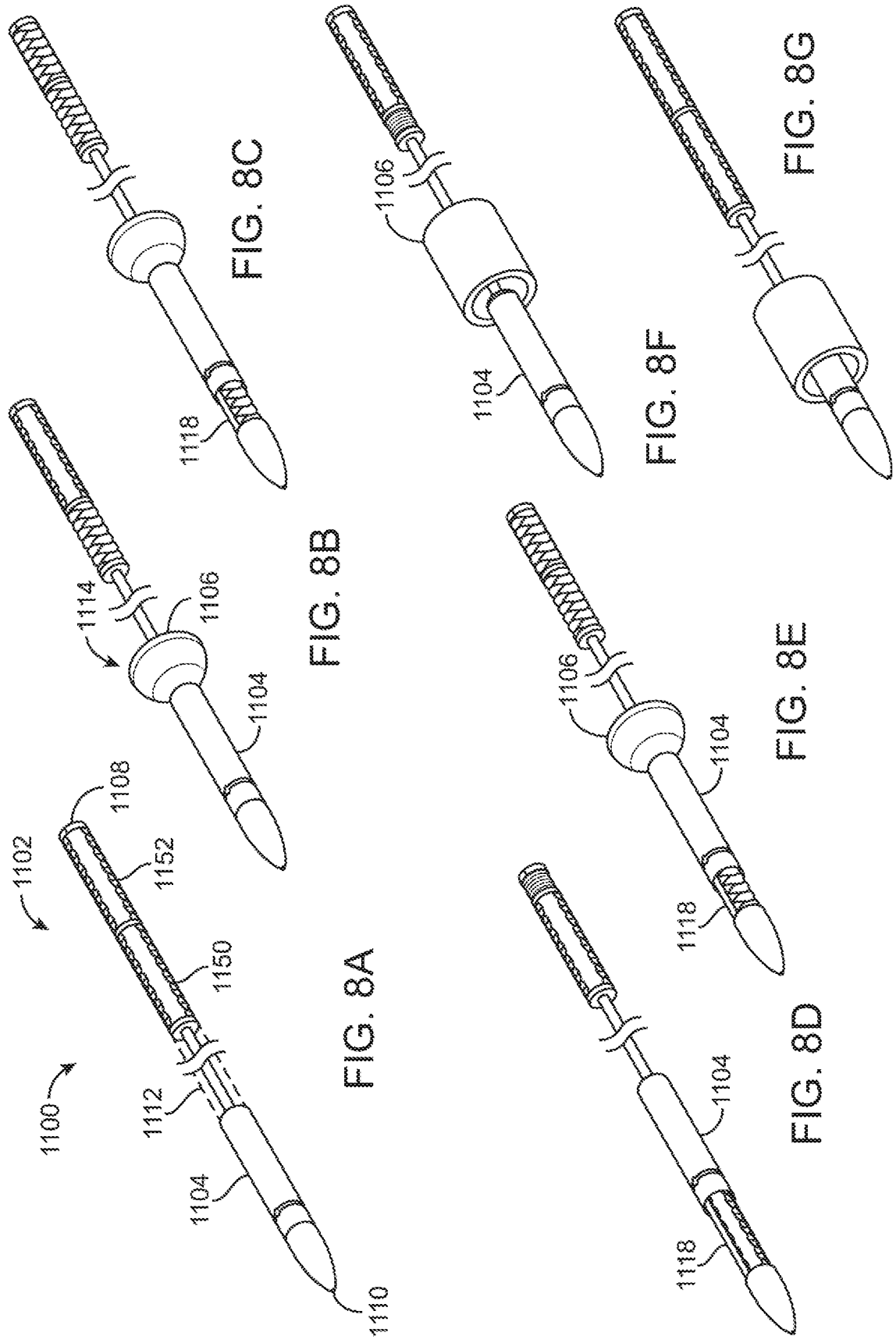

DETAIL V

SECTION A-A

DETAIL B

DETAIL C

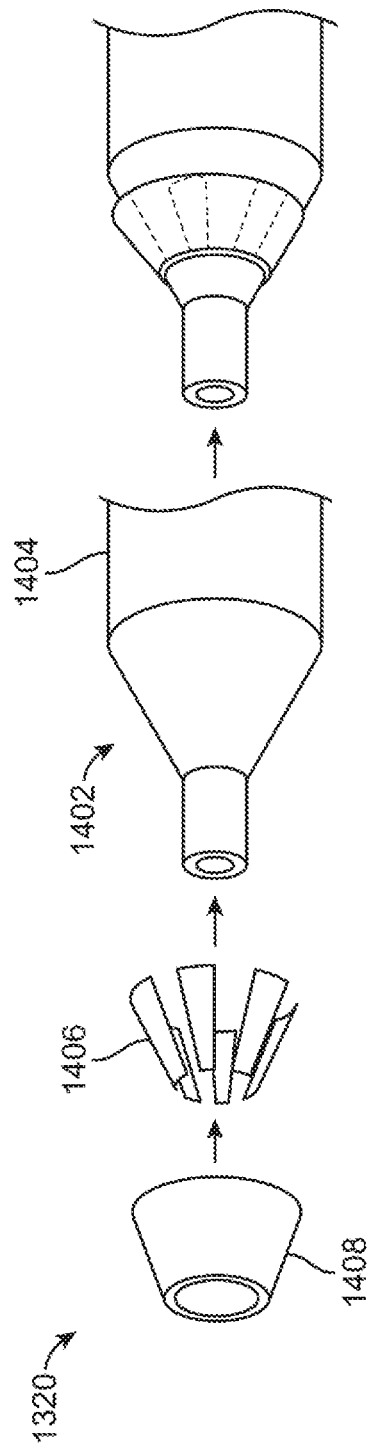
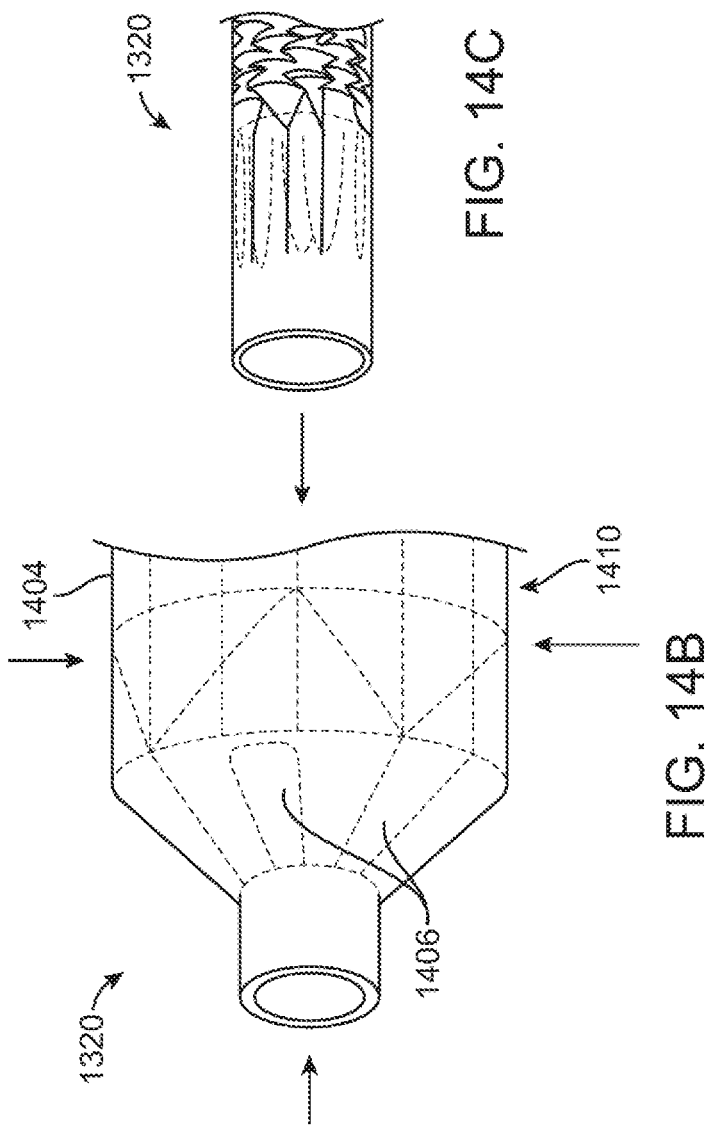
FIG. 14A
FIG. 14B
FIG. 14C

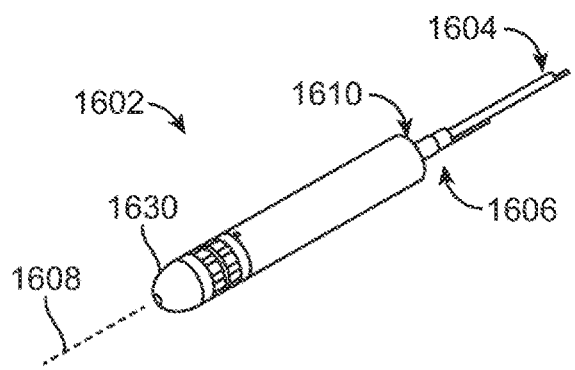
FIG. 16A
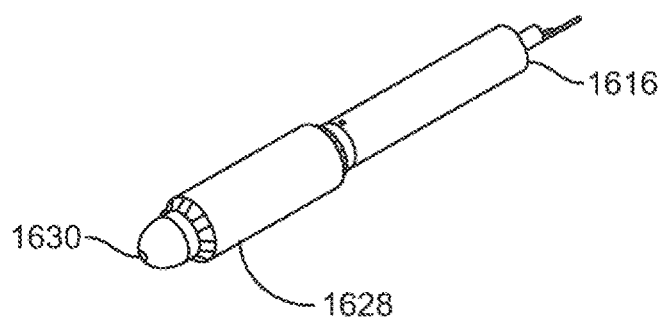
FIG. 16B
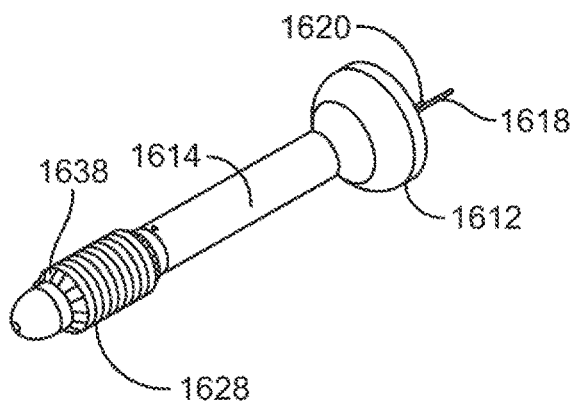
FIG. 16C
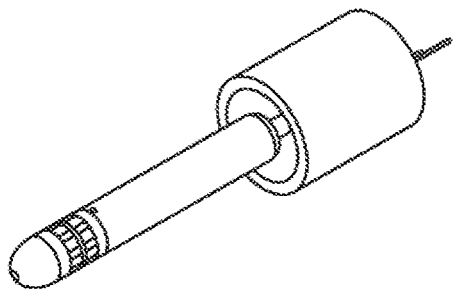
FIG. 16D
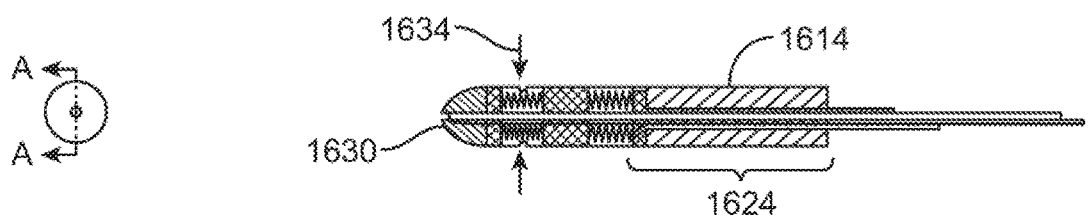
FIG. 16E-1
SECTION A-A
FIG. 16E-2

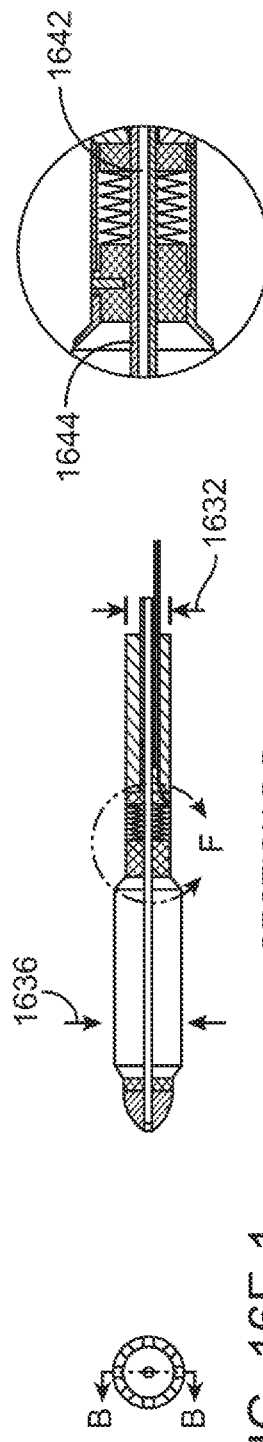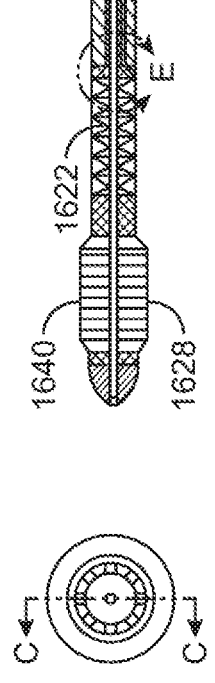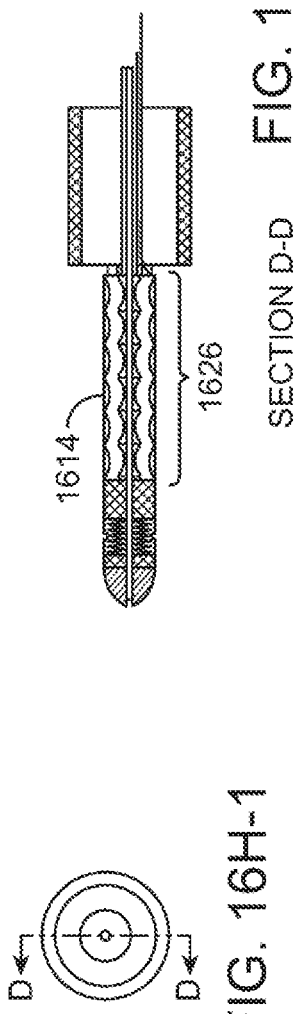

FIG. 17A
FIG. 17B
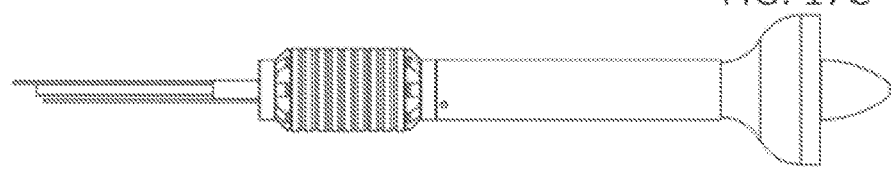
FIG. 17C
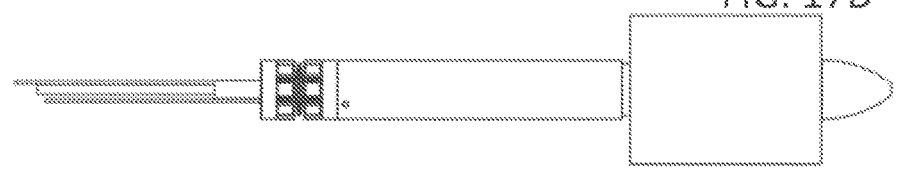
FIG. 17D
FIG. 17E-1
FIG. 17E-2
SECTION A-A
FIG. 17F-1
FIG. 17F-2
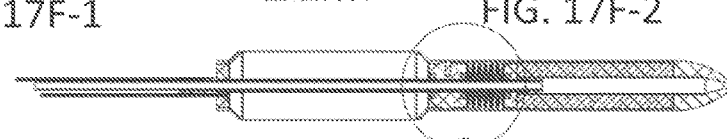
SECTION B-B
FIG. 17F-3
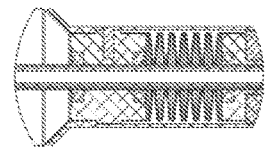
FIG. 17G-1
FIG. 17G-2
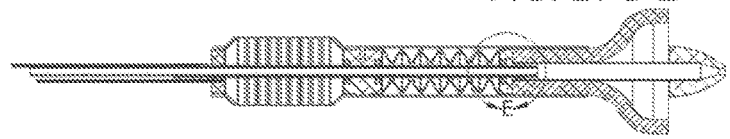
SECTION C-C
FIG. 17G-3
FIG. 17H-1
FIG. 17H-2
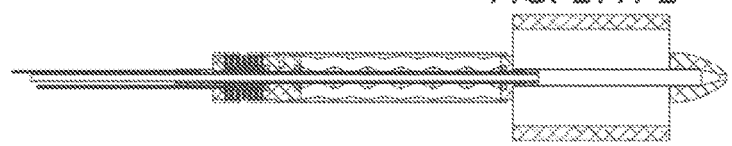
SECTION D-D

FLUID-ACTUATED DISPLACEMENT FOR CATHETERS, CONTINUUM MANIPULATORS, AND OTHER USES

CROSS REFERENCE TO RELATED APPLICATIONS

The present application is a continuation of PCT/US2019/013942 filed Jan. 17, 2019; which claims the benefit of U.S. Provisional Appln No. 62/618,551 filed Jan. 17, 2018; and is a continuation-in-part of U.S. application Ser. No. 15/469,085 filed Mar. 24, 2017 (Allowed); which claims the benefit of U.S. Provisional Appln No. 62/313,390 filed Mar. 25, 2016; the full disclosures which are incorporated herein by reference in their entirety for all purposes.

The subject matter of the present application is related to that of co-assigned U.S. application Ser. No. 15/081,026 entitled "Articulation Systems, Devices, and Methods for Catheters and Other Uses;" Ser. No. 15/080,979 entitled "Fluid Drive System for Catheter Articulation and Other Uses;" and Ser. No. 15/080,949 entitled "Fluid-Expandable Body Articulation of Catheters and Other Flexible Structures;" all filed on Mar. 25, 2016; the full disclosures which are also incorporated herein by reference in their entirety for all purposes.

FIELD OF THE INVENTION

In exemplary embodiments, the present invention provides structures, systems, and methods for selectively axially actuating or altering the lengths of catheters and other elongate flexible bodies, and the like. Particularly advantageous embodiments described herein can use fluid-driven actuators (optionally in the form of balloons) to (among other uses) axially displace a sheath from over a tool mounted on the end of a catheter or other elongate flexible body, for example, so as to release a self-expanding endoluminal prosthesis within the cardiovascular system of a patient. The invention also provides improved medical devices, systems, and method, with more specific embodiments providing improved articulated medical systems having a fluid-driven balloon array that can help shape, steer and/or advance a catheter, guidewire, or other elongate flexible structure along a body lumen. Alternative embodiments make use of balloon arrays distributed along single or multi-lumen shafts for improving the articulation behavior of a wide range of continuum robotic structures, flexible manipulators and/or end effectors, industrial robots, borescopes, prosthetic fingers, robotic arms, positioning supports or legs, consumer products, or the like.

BACKGROUND OF THE INVENTION

Diagnosing and treating disease often involve accessing internal tissues of the human body. Once the tissues have been accessed, medical technology offers a wide range of diagnostic tools to evaluate tissues and identify lesions or disease states. Similarly, a number of therapeutic tools have been developed that can help surgeons interact with, remodel, deliver drugs to, or remove tissues associated with a disease state so as to improve the health and quality of life of the patient. Unfortunately, gaining access to and aligning tools with the appropriate internal tissues for evaluation or treatment can represent a significant challenge to the physician, can cause serious pain to the patient, and may (at least in the near term) be seriously detrimental to the patient's health.

Open surgery is often the most straightforward approach for gaining access to internal tissues. Open surgery can provide such access by incising and displacing overlying tissues so as to allow the surgeon to manually interact with the target internal tissue structures of the body. This standard approach often makes use of simple, hand-held tools such as scalpels, clamps, sutures, and the like. Open surgery remains, for many conditions, a preferred approach. Although open surgical techniques have been highly successful, they can impose significant trauma to collateral tissues, with much of that trauma being associated with gaining access to the tissues to be treated.

To help avoid the trauma associated with open surgery, a number of minimally invasive surgical access and treatment technologies have been developed. Many minimally invasive techniques involve accessing the vasculature, often through the skin of the thigh, neck, or arm. One or more elongate flexible catheter structures can then be advanced along the network of blood vessel lumens extending throughout the body and its organs. While generally limiting trauma to the patient, catheter-based endoluminal therapies are often reliant on a number of specialized catheter manipulation techniques to safely and accurately gain access to a target region, to position a particular catheter-based tool in alignment with a particular target tissue, and/or to activate or use the tool. In fact, some endoluminal techniques that are relatively simple in concept can be very challenging (or even impossible) in practice (depending on the anatomy of a particular patient and the skill of a particular physician). More specifically, advancing a flexible guidewire and/or catheter through a tortuously branched network of body lumens might be compared to pushing a rope. As the flexible elongate body advances around first one curve and then another, and through a series of branch intersections, the catheter/tissue forces, resilient energy storage (by the tissue and the elongate body), and movement interactions may become more complex and unpredictable, and control over the rotational and axial position of the distal end of a catheter can become more challenging and less precise. Hence, accurately aligning these elongate flexible devices with the desired luminal pathway and target tissues can be a significant challenge.

A variety of mechanisms can be employed to steer or variably alter deflection of a tip of a guidewire or catheter in one or more lateral directions to facilitate endoluminal and other minimally invasive techniques. Pull wires may be the most common catheter tip deflection structures and work well for many catheter systems by, for example, controllably decreasing separation between loops along one side of a helical coil, braid, or cut hypotube near the end of a catheter or wire. It is often desirable to provide positive deflection in opposed directions (generally by including opposed pull wires), and in many cases along two orthogonal lateral axes (so that three or four pull wires are included in some devices). Where additional steering capabilities are desired in a single device, still more pull wires may be included. Complex and specialized catheter systems having dozens of pull wires have been proposed and built, in some cases with each pull wire being articulated by a dedicated motor attached to the proximal end. Alternative articulation systems have also been proposed, including electrically actuated shape memory alloy structures, piezoelectric actuation, phase change actuation, and the like. As the capabilities of steerable systems increase, the range of therapies that can use these technologies should continue to expand.

Unfortunately, as articulation systems for catheters get more complex, it can be more and more challenging to maintain accurate control over these flexible bodies. For example, pull wires that pass through bent flexible catheters often slide around the bends over surfaces within the catheter, with the sliding interaction extending around not only bends intentionally commanded by the user, but also around bends that are imposed by the tissues surrounding the catheter. Even after a diagnostic or therapeutic tool is positioned in alignment with a target tissue, it can be difficult to maintain that alignment while deploying or using the tool. For example, withdrawing a sheath proximally from over a self-expanding endoluminal prosthesis (such as a stent, valve, stent-graft, or the like) using standard techniques can involve applying many pounds of force to the portion of the deployment system that extends outside the patient. The combination of pulling the sheath proximally while pushing distally against a tool-supporting catheter shaft can make it difficult to maintain tool positioning inside the patient. Hence, there could be benefits to providing improved flexible body articulation behavior, and particularly to providing more accurate small and precise motions, to improving the lag time, and/or to providing improved transmission of motion over known catheter pull-wire systems so as to avoid compromising the positioning and coordination, as experienced by the surgeon, between the input and output of catheters and other elongate flexible tools.

Along with catheter-based therapies, a number of additional minimally invasive surgical technologies have been developed to help treat internal tissues while avoiding at least some of the trauma associated with open surgery. Among the most impressive of these technologies is robotic surgery. Robotic surgeries often involve inserting one end of an elongate rigid shaft into a patient, and moving the other end with a computer-controlled robotic linkage so that the shaft pivots about a minimally invasive aperture. Surgical tools can be mounted on the distal ends of the shafts so that they move within the body, and the surgeon can remotely position and manipulate these tools by moving input devices with reference to an image captured by a camera from within the same workspace, thereby allowing precisely scaled micro-surgery. Alternative robotic systems have also been proposed for manipulation of the proximal end of flexible catheter bodies from outside the patient so as to position distal treatment tools. These attempts to provide automated catheter control have met with challenges, which may be in-part because of the difficulties in providing accurate control at the distal end of a flexible elongate body using pull-wires extending along bending body lumens. Still further alternative catheter control systems apply large magnetic fields using coils outside the patient's body to direct catheters inside the heart of the patient, and more recent proposals seek to combine magnetic and robotic catheter control techniques. While the potential improvements to surgical accuracy make all of these efforts alluring, the capital equipment costs and overall burden to the healthcare system of these large, specialized systems is a concern.

In light of the above, it would be beneficial to provide improved articulation systems and devices, methods of articulation, and methods for making articulation structures. Improved techniques for controlling the bending of elongate structures (articulated or non-articulated) would also be beneficial. It would be particularly beneficial if these new technologies were suitable to provide therapeutically effective control over actuation and/or movement of a distal end of a flexible guidewire, catheter, or other elongate body extending into a patient body, optionally for deployment of therapeutic tools such as by axially sliding a sheath from over a self-expanding prosthetic valve. It would also be beneficial if the movement provided by these new techniques would allow enhanced ease of use. It would also be helpful if these techniques could provide improved motion and control capabilities for a wide range of distinct medical and industrial devices.

BRIEF SUMMARY OF THE INVENTION

The present invention generally provides improved medical devices, systems, and methods, and also provides structures and techniques for improving the behavior of flexible and/or articulated structures such as continuum robotic manipulators, pull-wire catheters, and the like. Catheter-supported therapeutic and diagnostic tools can be introduced into a patient body with a sheath slidably disposed over the tool. Once the tool is aligned with a target tissue, a fluid-driven actuator can move the sheath axially from over the tool, for example, to allow a stent, stent-graft, prosthetic valve, or the like to expand radially within the cardiovascular system, without having to transmit large deployment forces along the catheter shaft and sheath from outside the patient.

In a first aspect, the invention provides a catheter-based tool deployment system comprising an elongate flexible catheter body having a proximal end and a distal portion with an axis therebetween. A receptacle for receiving a therapeutic or diagnostic tool is along the distal portion of the catheter body, and a tubular sheath has a lumen slidably receiving the distal portion of the catheter therein. A first fluid channel and a second fluid channel extend axially along the catheter body. A first actuator is disposed along the distal portion in fluid communication with the first channel. The first actuator couples the distal portion with the sheath so that, in response to fluid transmitted along the first channel, the first actuator drives the sheath axially between a first position over the receptacle and a second position axially offset from the first position such that the tool is uncovered for use. A second actuator is in fluid communication with the second channel, and the second actuator axially couples the distal portion of the catheter with the sheath so that transmission of inflation fluid along the second channel drives the sheath axially in opposition to the first actuator, and so as to extend a distal end of the catheter body distally relative to the receptacle.

In another aspect, the invention provides a catheter-based prosthetic heart valve deployment system comprising an elongate flexible catheter body having a proximal end and a distal portion with an axis therebetween. The distal portion is configured for supporting a prosthetic heart valve. A tubular sheath has a lumen slidably receiving the distal portion therein. The sheath has an outer profile. A first fluid channel extends axially along the catheter body. A first balloon is in fluid communication with the first channel and axially couples the distal portion of the catheter body with the sheath so that when inflation fluid is transmitted along the first channel the first balloon drives the sheath axially between a first position and a second position. The first balloon is inflatable from an insertion profile to an inflated profile larger than the sheath profile.

In a method aspect, the invention provides a method for deploying a catheter-based tool. The method comprises introducing an elongate flexible catheter body distally into a patient body. The distal portion supports a tool. Fluid is transmitted distally from outside the patient into a first channel extending along the catheter body. A balloon is expanded radially and a tubular sheath is driven over the distal portion between a first position (over the tool) and a second position with the transmitted fluid, wherein the radial expanding of the balloon increases a profile of the balloon to an inflated profile larger than the sheath.

A number of general features may be beneficial for some or all of the aspects of the invention provided herein. For example, the tubular sheath may have an outer cross-sectional profile, and the second actuator can comprise a balloon expandable from an uninflated configuration having an uninflated cross-sectional profile to an inflated configuration having an inflated cross-sectional profile, typically in response to the transmission of inflation fluid along the second channel. The inflated cross-sectional profile may be larger than the sheath profile, and the uninflated profile may be smaller than, or about the same size as, the sheath profile. Separately, the balloon in the uninflated configuration has an uninflated axial length, and the balloon in the inflated configuration can have an inflated axial length greater than the uninflated axial length. The balloon can axially couple the distal portion of the catheter with the sheath so that transmission of inflation fluid along the second channel extends a distal end of the catheter body distally relative to the receptacle. Optionally, the first actuator comprises a first balloon and the balloon of the second actuator comprises a second balloon. The second balloon can be distal of the first balloon and the first balloon can be distal of the receptacle.

Preferably, a tension member extends axially along the first and second actuators. The tension member can limit distal elongation of the end of the catheter during inflation of the second balloon so that transmission of the inflation fluid distally along the first channel can drive the inflation fluid from the second actuator proximally along the second channel, and so that transmission of the inflation fluid distally along the second channel can drive the inflation fluid from the first actuator proximally along the first channel. Optionally, the tension member elongates axially from a first tension member configuration to a second tension member configuration in response to transmission of the inflation fluid, and the tension member may inhibit elongation beyond the second tension member configuration so as to facilitate driving the sheath back over the receptacle. The tension member may comprise an inner tubular shaft and an outer tubular shaft slidingly receiving the inner shaft therein, with a stop inhibiting telescoping elongation of the shafts beyond the second tension member configuration. The shafts may comprise metal or a rigid polymer, optionally comprising stainless steel. In an advantageous arrangement, the first channel is disposed between the outer tubular shaft and an intermediate tubular shaft, the outer shaft is axially affixed to the tool receptacle, and the second channel is disposed between the inner shaft and the intermediate shaft. The tension member may include corresponding features that axially couple the inner shaft to the outer shaft so as to limit axial sliding.

The first actuator, the second actuator, or both may comprise an axially segmented balloon having a balloon axis extending along the axis of the catheter body. A first end of the balloon may be axially coupled with the receptacle and a second end axially coupled with the sheath so that inflation pressure against the ends increases an axial length of the balloon and drives the sheath. The segmented balloon can have an outer wall with a plurality of radial members extending radially inwardly from the wall toward a shaft of the catheter body, the shaft extending axially within the balloon. Optionally, the distal portion of the catheter body has a lumen slidably receiving a shaft, a distal end of the shaft being affixed to a distal end of the sheath. A seal can be maintained between the shaft and the catheter body when the sheath moves between the first position and the second position. To improve performance, the second actuator may comprise a balloon having a proximal end and a distal end, and the structure may further comprise a plurality of reinforcing struts extending radially along the proximal balloon end, the distal balloon end, or both so as to facilitate transmission of axial balloon actuation forces between the catheter body and the sheath.

In another aspect, the invention provides a catheter-based tool deployment system comprising an elongate flexible catheter body having a proximal end and a distal portion with an axis therebetween. A receptacle for a therapeutic or diagnostic tool is included along the distal portion of the catheter body. A tubular sheath has a lumen that can slide over the distal portion of the catheter. A first fluid channel extends axially along the catheter body, and a first actuator is disposed along the distal portion in fluid communication with the first channel. The first actuator couples the distal portion with the sheath so that, in response to fluid transmitted along the first channel, the first actuator drives the sheath axially between a first position (extending over the receptacle) and a second position (axially offset from the first position such that the tool is uncovered for use).

The systems, devices, and methods described herein may further include one or more of a number of different general features. For example, the tool may comprise an endoluminal implant biased to expand from a small profile configuration to a large profile configuration. The sheath can be configured to radially constrain the implant when the sheath is in the first position, and to slide axially over the implant from the first position toward the second position so as to radially release the implant, optionally within a cardiovascular system of a patient. The tool may optionally comprise a prosthetic valve, often a prosthetic mitral valve. A wide variety of alternative tools may be supportable by the catheter body, with the tool typically being releasably held in the receptacle, although some sheathed tools may be fixed in place. The distal portion of the catheter body may comprise an articulated segment disposed proximally of the receptacle. The distal portion of the catheter body, can, for example, have a plurality of articulated segments configured to position and orient the valve (or other tool) with at least 3 degrees of freedom, with the articulated segment ideally including an articulation balloon array (though other articulation actuators could be used, including pull-wires). Counterintuitively, the second position of the sheath may be distal of the first position so that the sheath moves distally and away from bends of the catheter body disposed between the receptacle and the proximal end when uncovering the tool for use. Regardless, a fluid-driven balloon, bellows, piston, or other actuator can generate significant sheath actuation forces locally (often 3 lb or more, often being 5 or even 10 lb or more, and in some cases being 15 lb or more) sufficiently near where the sheath is to be moved from over the tool so that as to avoid any need for transmitting these forces around bends of the elongate catheter system associated with tortuosity of the vasculature or other body lumen access pathway.

The sheath actuation devices, systems, and methods described herein may benefit from any of a number of additional technologies and features. Optionally, the first actuator comprises a first balloon. The transmission of the fluid can inflate the first balloon from an uninflated configuration to an inflated configuration. The first balloon in the uninflated configuration can have an uninflated axial length, and the first balloon in the inflated configuration can have an inflated axial length that is greater than the uninflated axial length. Somewhat surprisingly, the first balloon can be distal of the tool and the inflation state of the balloon may help define an overall length of the catheter system. Hence, expansion of the first balloon from the first axial length to the second axial length may extend a distal end of the catheter system distally relative to the receptacle.

Where, for example, both deployment and retrieval are desired a second actuator may be in fluid communication with a second channel extending along the catheter body, and the second actuator can axially couple the distal portion of the catheter with the sheath so that transmission of inflation fluid along the second channel drives the sheath axially away from the second position and toward the first position. The second actuator may comprise a second balloon, and the transmission of the fluid along the second channel can inflate the second balloon from an uninflated configuration to an elongate inflated configuration. Optionally, the second balloon is distal of the first balloon, and a tension member extends axially along the first and second balloons to limit a total combined length of the two balloons and distal advancement of the end of the catheter during inflation of the second balloon so that axial elongation of the second balloon drives the first balloon and the sheath proximally toward the first position.

The first channel is optionally disposed between an outer tubular shaft and an intermediate tubular shaft. The outer shaft can be axially affixed to the tool receptacle so as to form a structure of the catheter body, and the second channel can be disposed between an inner shaft and the intermediate shaft. The tension member can axially couple the inner shaft to the outer shaft. The intermediate shaft and inner shaft may optionally extend proximally beyond the proximal end of the catheter body, and a third balloon that is in fluid communication with the first channel can also be included. A fourth balloon in fluid communication with the second channel may similarly be included, and the third balloon may axially couple the intermediate shaft with the outer shaft, with the fourth balloon axially coupling the intermediate shaft with the inner shaft. The balloons can have axially oriented ends coupled to the shafts so that distally driving a proximal portion of the inner shaft relative to the intermediate shaft shortens the first balloon and drives inflation fluid along the first channel so as to inflate the first balloon. Similarly, distally driving a proximal portion of the intermediate shaft relative to the outer shaft shortens the fourth balloon and drives inflation fluid along the second channel so as to inflate the second balloon. One, some, or all of the sheath actuation balloons can have a first plurality of laterally opposed folds extending transverse to the axis and a second plurality of laterally opposed folds circumferentially offset from the first folds. Alternative balloon fold arrangements can also be employed, including having a series of bellows-like folds, a helical folding pattern, or the like.

Optionally, the distal portion of the catheter body has a lumen slidably receiving a shaft, and a distal end of the shaft is affixed to a distal end of the sheath. A proximal end of the first balloon can be affixed to the catheter body, and a distal end of the first balloon can be affixed to the shaft. A seal is maintained between the shaft and the catheter body when the sheath moves between the first position and the second position, for example, using an axially elongateable balloon wall to function as the seal. Alternative seal structures can also be used, including an o-ring or other annular body sliding against the shaft or catheter body, an evertable sleeve extending axially in an annular space between the shaft and catheter body, or the like. In still further alternative arrangements described herein, the sleeve actuator comprises a first balloon, and an opposed balloon is also provided. Alternating inflation of the first balloon and the opposed balloon can incrementally drive the sheath axially. In some embodiments, alternating balloon systems can selectably uncover or recover a tool, such as by including a balloon-actuated clutch to selectably drive a sheath proximally or distally.

In another aspect the invention provides a catheter-based prosthetic heart valve deployment system comprising an elongate flexible catheter body having a proximal end and a distal portion with an axis therebetween. The distal portion is configured for supporting a prosthetic heart valve. A tubular sheath has a lumen slidably receiving the distal portion therein. A first fluid channel extends axially along the catheter body. A first balloon is in fluid communication with the first channel and axially couples the distal portion of the catheter body with the sheath so that when inflation fluid is transmitted along the first channel the first balloon drives the sheath axially or rotationally between a first position and a second position.

In another aspect, the invention provides a method for deploying a catheter-based tool. The method comprises introducing an elongate flexible catheter body distally into a patient body, the distal portion supporting a tool. Fluid is transmitted distally from outside the patient into a first channel extending along the catheter body, and a tubular sheath is driven over the distal portion, between a first position over the tool and a second position, by the transmitted fluid.

BRIEF DESCRIPTION OF THE DRAWINGS

FIG. 1-1 schematically illustrates a catheter articulation system having a hand-held proximal housing and a catheter with a distal articulatable portion in a relaxed state.

FIGS. 7A-7E-2 illustrate components of another alternative elongate articulated flexible structure having axial expansion balloons.

FIGS. 8A-8G are perspective illustrations of a prosthetic heart valve delivery system having a fluid-driven sheath actuation system, showing how inflation of balloon actuators can generate forces within a patient body so as to move a sheath over a self-expanding heart valve to partially deploy the valve, recapture the valve, and fully deploy the valve, and also showing how actuation can be driven using a proximal balloon system to generate controlled fluid flows and help move fluid transmission shafts from outside the patient.

FIG. 14A is a schematic exploded view showing attachment of a circumferential series of reinforcing struts along an end of an axial articulation balloon to as to facilitate transmission of axial forces FIGS. 14B and 14C are schematic illustrations of an axial articulation balloon having reinforcing struts along the end, with the balloon shown in an inflated configuration and in a radially and axially compressed configuration, respectively.

FIGS. 16A-16H-2 illustrate a fluid actuated prosthetic mitral valve deployment and retrieval system related to that of FIGS. 8A-11D, with the recapture balloon having an inflated profile that is larger than that of the sheath used to radially constrain the valve during insertion and positioning, along with methods for using the opposed balloons of the system to controllably deploy and recapture the.

FIGS. 17A-17H-2 illustrate an alternative large-balloon mitral valve deployment and retrieval system structure and method for its use that are related to that of FIGS. 16A-17H-2, with the deployment being performed by withdrawing the sheath proximally, and in which the opposed balloon system can be used to axially advance and position the prosthetic valve relative to the native valve tissue prior to deployment.

DETAILED DESCRIPTION OF THE INVENTION

Figure 1:
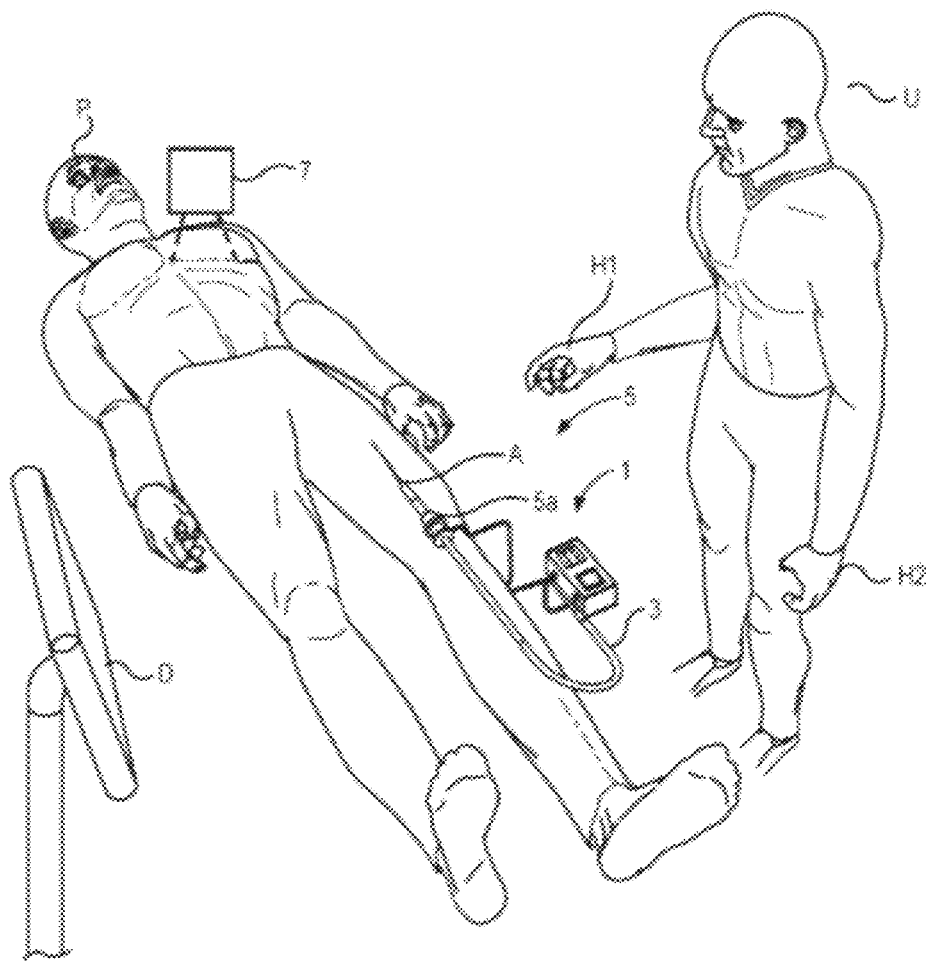
FIG. 1 is a simplified perspective view of a medical procedure in which a physician can input commands into a catheter system so that a catheter is articulated using systems and devices described herein.
Figure 1:
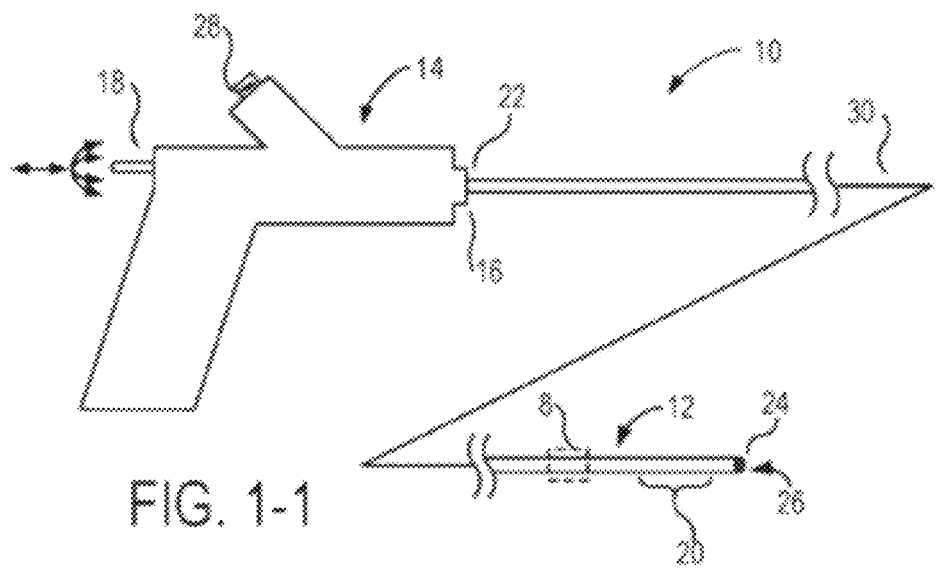

The present invention generally provides fluid control devices, systems, and methods that are particularly useful for articulating catheters and other elongate flexible structures. In exemplary embodiments the invention provides a modular manifold architecture that includes plate-mounted valves to facilitate fluid communication along a plurality of fluid channels included in one or more multi-lumen shafts, often for articulating actuators of a catheter. Preferred actuators include balloons or other fluid-expandable bodies, and the modular manifold assemblies are particularly well suited for independently controlling a relatively large number of fluid pressures and/or flows. The individual plate modules may include valves that control fluid supplied to a catheter or other device, and/or fluid exhausted from the catheter or other device. A receptacle extending across a stack of such modules can receive a fluid flow interface having a large number of individual fluid coupling ports, with the total volume of the modular valve assembly, including the paired receptacle and fluid flow interface of the device often being quite small. In fact, the modular manifold will preferably be small enough to hold in a single hand, even when a controller (such as a digital processor), a pressurized fluid source (such as a canister of cryogenic fluid), and an electrical power source (such as a battery) are included. When used to transmit liquids that will vaporize to a gas that inflates a selected subset of microballoons within a microballoon array, control over the small quantities of inflation liquids may direct microfluidic quantities of inflation fluids. Microelectromechanical system (MEMS) valves and sensors may find advantageous use in these systems; fortunately, suitable microfluidic and MEMS structures are now commercially available and/or known valve structures may be tailored for the applications described herein by a number of commercial service providers and suppliers.

The catheter bodies (and many of the other elongate flexible bodies that benefit from the inventions described herein) will often be described herein as having or defining an axis, such that the axis extends along the elongate length of the body. As the bodies are flexible, the local orientation of this axis may vary along the length of the body, and while the axis will often be a central axis defined at or near a center of a cross-section of the body, eccentric axes near an outer surface of the body might also be used. It should be understood, for example, that an elongate structure that extends "along an axis" may have its longest dimension extending in an orientation that has a significant axial component, but the length of that structure need not be precisely parallel to the axis. Similarly, an elongate structure that extends "primarily along the axis" and the like will generally have a length that extends along an orientation that has a greater axial component than components in other orientations orthogonal to the axis. Other orientations may be defined relative to the axis of the body, including orientations that are transvers to the axis (which will encompass orientation that generally extend across the axis, but need not be orthogonal to the axis), orientations that are lateral to the axis (which will encompass orientations that have a significant radial component relative to the axis), orientations that are circumferential relative to the axis (which will encompass orientations that extend around the axis), and the like. The orientations of surfaces may be described herein by reference to the normal of the surface extending away from the structure underlying the surface. As an example, in a simple, solid cylindrical body that has an axis that extends from a proximal end of the body to the distal end of the body, the distal-most end of the body may be described as being distally oriented, the proximal end may be described as being proximally oriented, and the surface between the proximal and distal ends may be described as being radially oriented. As another example, an elongate helical structure extending axially around the above cylindrical body, with the helical structure comprising a wire with a square cross section wrapped around the cylinder at a 20 degree angle, might be described herein as having two opposed axial surfaces (with one being primarily proximally oriented, one being primarily distally oriented). The outermost surface of that wire might be described as being oriented exactly radially outwardly, while the opposed inner surface of the wire might be described as being oriented radially inwardly, and so forth.

Referring first to FIG. 1, a first exemplary catheter system 1 and method for its use are shown. A physician or other system user U interacts with catheter system 1 so as to perform a therapeutic and/or diagnostic procedure on a patient P, with at least a portion of the procedure being performed by advancing a catheter 3 into a body lumen and aligning an end portion of the catheter with a target tissue of the patient. More specifically, a distal end of catheter 3 is inserted into the patient through an access site A, and is advanced through one of the lumen systems of the body (typically the vasculature network) while user U guides the catheter with reference to images of the catheter and the tissues of the body obtained by a remote imaging system.

Exemplary catheter system 1 will often be introduced into patient P through one of the major blood vessels of the leg, arm, neck, or the like. A variety of known vascular access techniques may also be used, or the system may alternatively be inserted through a body orifice or otherwise enter into any of a number of alternative body lumens. The imaging system will generally include an image capture system 7 for acquiring the remote image data and a display D for presenting images of the internal tissues and adjacent catheter system components. Suitable imaging modalities may include fluoroscopy, computed tomography, magnetic resonance imaging, ultrasonography, combinations of two or more of these, or others.

Catheter 3 may be used by user U in different modes during a single procedure, including two or more of a manual manipulation mode, an automated and powered shape-changing mode, and a combination mode in which the user manually moves the proximal end while a computer articulates the distal portion. More specifically, at least a portion of the distal advancement of catheter 3 within the patient may be performed in a manual mode, with system user U manually manipulating the exposed proximal portion of the catheter relative to the patient using hands H1, H2. Catheter 3 may, for example, be manually advanced over a guidewire, using either over-the-wire or rapid exchange techniques. Catheter 3 may also be self-guiding during manual advancement (so that for at least a portion of the advancement of catheter 3, a distal tip of the catheter may guide manual distal advancement). Automated lateral deflection of a distal portion of the catheter may impose a desired distal steering bend prior to a manual movement, such as near a vessel bifurcation, followed by manual movement through the bifurcation. In addition to such manual movement modes, catheter system 1 may also have a 3-D automated movement mode using computer controlled articulation of at least a portion of the length of catheter 3 disposed within the body of the patient to change the shape of the catheter portion, often to advance or position the distal end of the catheter. Movement of the distal end of the catheter within the body will often be provided per real-time or near real-time movement commands input by user U, with the portion of the catheter that changes shape optionally being entirely within the patient so that the movement of the distal portion of the catheter is provided without movement of a shaft or cable extending through the access site. Still further modes of operation of system 1 may also be implemented, including concurrent manual manipulation with automated articulation, for example, with user U manually advancing the proximal shaft through access site A while computer-controlled lateral deflections and/or changes in stiffness over a distal portion of the catheter help the distal end follow a desired path or reduce resistance to the axial movement.

Referring next to FIG. 1-1 components which may be included in or used with catheter system 1 or catheter 3 (described above) can be more fully understood with reference to an alternative catheter system 10 and its catheter 12. Catheter 12 generally includes an elongate flexible catheter body and is detachably coupled to a handle 14, preferably by a quick-disconnect coupler 16. Catheter body 12 has an axis 30, and an input 18 of handle 14 can be moved by a user so as to locally alter the axial bending characteristics along catheter body 12, often for variably articulating an actuated portion 20 of the catheter body. Catheter body 12 will often have a working lumen 26 into or through which a therapeutic and/or diagnostic tool may be advanced from a proximal port 28 of handle 14. Alternative embodiments may lack a working lumen, may have one or more therapeutic or diagnostic tools incorporated into the catheter body near or along actuated portion 20, may have a sufficiently small outer profile to facilitate use of the body as a guidewire, may carry a tool or implant near actuated portion 20 or near distal end 26, or the like. In particular embodiments, catheter body 12 may support a therapeutic or diagnostic tool 8 proximal of, along the length of, and/or distal of actuated portion 20. Alternatively, a separate elongate flexible catheter body may be guided distally to a target site once catheter body 20 has been advanced (with the elongate body for such uses often taking the form and use of a guidewire or guide catheter).

The particular tool or tools included in, advanceable over, and/or introducible through the working lumen of catheter body 20 may include any of a wide range of therapeutic and/or treatment structures. Examples include cardiovascular therapy and diagnosis tools (such as angioplasty balloons, stent deployment balloons or other devices, atherectomy devices, tools for detecting, measuring, and/or characterizing plaque or other occlusions, tools for imaging or other evaluation of, and/or treatment of, the coronary or peripheral arteries, structural heart tools (including prostheses or other tools for valve procedures, for altering the morphology of the heart tissues, chambers, and appendages, and the like), tools for electrophysiology mapping or ablation tools, and the like); stimulation electrodes or electrode implantation tools (such as leads, lead implant devices, and lead deployment systems, leadless pacemakers and associated deployments systems, and the like); neurovascular therapy tools (including for accessing, diagnosis and/or treatment of hemorrhagic or ischemic strokes and other conditions, and the like); gastrointestinal and/or reproductive procedure tools (such as colonoscopic diagnoses and intervention tools, transurethral procedure tools, transesophageal procedure tools, endoscopic bariatric procedure tools, etc.); hysteroscopic and/or falloposcopic procedure tools, and the like; pulmonary procedure tools for therapies involving the airways and/or vasculature of the lungs; tools for diagnosis and/or treatment of the sinus, throat, mouth, or other cavities, and a wide variety of other endoluminal therapies and diagnoses structures. Such tools may make use of known surface or tissue volume imaging technologies (including imaging technologies such as 2-D or 3-D cameras or other imaging technologies; optical coherence tomography technologies; ultrasound technologies such as intravascular ultrasound, transesophogeal ultrasound, intracardiac ultrasound, Doppler ultrasound, or the like; magnetic resonance imaging technologies; and the like), tissue or other material removal, incising, and/or penetrating technologies (such a rotational or axial atherectomy technologies; morcellation technologies; biopsy technologies; deployable needle or microneedle technologies; thrombus capture technologies; snares; and the like), tissue dilation technologies (such as compliant or non-compliant balloons, plastically or resiliently expandable stents, reversibly expandable coils, braids or other scaffolds, and the like), tissue remodeling and/or energy delivery technologies (such as electrosurgical ablation technologies, RF electrodes, microwave antennae, cautery surfaces, cryosurgical technologies, laser energy transmitting surfaces, and the like), local agent delivery technologies (such as drug eluting stents, balloons, implants, or other bodies; contrast agent or drug injection ports; endoluminal repaving structures; and the like), implant and prosthesis deploying technologies, anastomosis technologies and technologies for applying clips or sutures, tissue grasping and manipulation technologies; and/or the like. In some embodiments, the outer surface of the articulation structure may be used to manipulate tissues directly. Other examples of surgical interventions which can impose significant collateral damage, and for which less-invasive endoluminal approaches may be beneficial, include treatments of the brain (including nerve stimulation electrode implantation, neurovascular therapies including for diagnosis and/or treatment of hemorrhagic or ischemic strokes and other conditions, and the like); cardiovascular therapies and diagnoses (including evaluation and/or treatments of the coronary or peripheral arteries, structural heart therapies such as valve procedures or closure of atrial appendages, electrophysiology procedures such as mapping and arrhythmia treatments, and the like); gastrointestinal and/or reproductive procedures (such as colonoscopic diagnoses and interventions, transurethral procedures, transesophageal procedures, endoscopic bariatric procedures, etc.); hysteroscopic and/or falloposcopic procedures, and the like; pulmonary procedures involving the airways and/or vasculature of the lungs; diagnosis and/or treatment of the sinus, throat, mouth, or other cavities, and a wide variety of other endoluminal therapies and diagnoses. Unfortunately, known structures used for different therapies and/or insertion into different body lumens are quite specialized, so that it will often be inappropriate (and possibly ineffective or even dangerous) to try to use a device developed for a particular treatment for another organ system. Non-medical embodiments may similarly have a wide range of tools or surfaces for industrial, assembly, imaging, manipulation, and other uses.

Addressing catheter body 12 of system 10 (and particularly articulation capabilities of actuated portion 20) in more detail, the catheter body generally has a proximal end 22 and a distal end 24 with axis 30 extending between the two. As can be understood with reference to FIG. 2, catheter body 12 may have a short actuated portion 20 of about 3 diameters or less, but will often have an elongate actuated portion 20 extending intermittently or continuously over several diameters of the catheter body (generally over more than 3 diameters, often over more than 10 diameters, in many cases over more than 20 diameters, and in some embodiments over more than 40 diameters). A total length of catheter body 12 (or other flexible articulated bodies employing the actuation components described herein) may be from 5 to 500 cm, more typically being from 15 to 260 cm, with the actuated portion optionally having a length of from 1 to 150 cm (more typically being 2 to 20 cm) and an outer diameter of from 0.65 mm to 5 cm (more typically being from 1 mm to 2 cm). Outer diameters of guidewire embodiments of the flexible bodies may be as small as 0.012" though many embodiments may be more than 2 Fr, with catheter and other medical embodiments optionally having outer diameters as large as 34 French or more, and with industrial robotic embodiments optionally having diameters of up to 1" or more. Exemplary catheter embodiments for structural heart therapies (such as trans-catheter aortic or mitral valve repair or implantation, left atrial appendage closure, and the like) may have actuated portions with lengths of from 3 to 30 cm, more typically being from 5 to 25 cm, and may have outer profiles of from 10 to 30 Fr or 10 to 40 Fr, typically being from 12 to 18 Fr, and ideally being from 13 to 16 Fr or from 16 to 24 Fr. Electrophysiology therapy catheters (including those having electrodes for sensing heart cycles and/or electrodes for ablating selected tissues of the heart) may have sizes of from about 5 to about 12 Fr, and articulated lengths of from about 3 to about 30 cm. A range of other sizes might also be implemented for these or other applications.

Figure 1A:
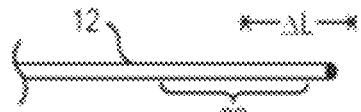
FIGS. 1A-1C schematically illustrate a plurality of alternative articulation states of the distal portion of the catheter in the system of FIG. 1.
Figure 1B:
Figure 1C:
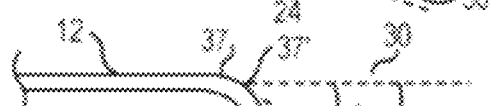

Referring now to FIGS. 1A, 1B, and 1C, system 10 may be configured to articulate actuated portion 20. Articulation will often allow movement continuously throughout a range of motion, though some embodiments may provide articulation in-part or in-full by selecting from among a plurality of discrete articulation states. Catheters having opposed axial extension and contraction actuators are described herein that may be particularly beneficial for providing continuous controlled and reversible movement, and can also be used to modulate the stiffness of a flexible structure. These continuous and discrete systems share many components (and some systems might employ a combination of both approaches).

Conveniently, the overall actuation configuration or state of catheter body 12 may be described using a plurality of scalar quantities that are each indicative of the states of associated actuation increments and balloons, with those incremental states optionally being combined to define an actuation state vector or matrix. Where the actuation increments are digital in nature (such as being associated with full inflation or full deflation of a balloon), some or all of the actuation state of catheter 12 may be described by a digital actuation state vector or matrix. Such digital embodiments (particularly those without analog components) may take advantage of these simple digital state vectors or digital state matrices to significantly facilitate data manipulations and enhance control signal processing speeds, helping to lessen minimum desired processing capabilities and overall system costs. Note also that many of the resolution, flexibility, and accuracy advantages of the balloon array systems described above are also available when all of the balloons of the array are inflatable to variable inflation states. Hence, some embodiments of the systems described herein may include fluid control systems that direct modulated quantities and/or pressures of fluids to multiple balloons along one or more fluid transmission channels. Control systems for such embodiments may employ similar processing approaches, but with the balloon inflation scalar values having variable values in a range from minimal or no effective inflation to fully inflated.

Figure 2:
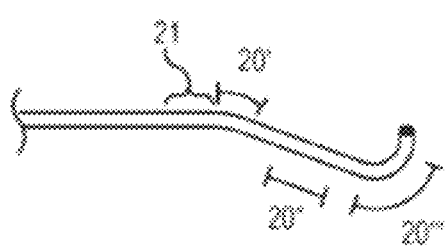
FIG. 2 schematically illustrates an alternative distal structure having a plurality of articulatable sub-regions or segments so as to provide a desired total number of degrees of freedom and range of movement.

Referring now to FIGS. 1-1 and 2, embodiments of articulation system 10 will move the distal end 24 of catheter 12 toward a desired position and/or orientation in a workspace relative to a base portion 21, with the base portion often being adjacent to and proximal of actuated portion 20. Note that such articulation may be relatively (or even completely) independent of any bending of catheter body 12 proximal of base portion 21. The location and orientation of proximal base 21 (relative to handle 14 or to another convenient fixed or movable reference frame) may be identified, for example, by including known catheter position and/or orientation identification systems in system 10, by including radiopaque or other high-contrast markers and associated imaging and position and/or orientation identifying image processing software in system 10, by including a flexible body state sensor system along the proximal portion of catheter body 12, by foregoing any flexible length of catheter body 12 between proximal handle 14 and actuated portion 20, or the like. A variety of different degrees of freedom may be provided by actuated portion 20. Exemplary embodiments of articulation system 10 may allow, for example, distal end 24 to be moved with 2 degrees of freedom, 3 degrees of freedom, 4 degrees of freedom, 5 degrees of freedom, or 6 degrees of freedom relative to base portion 21. The number of kinematic degrees of freedom of articulated portion 20 may be much higher in some embodiments, particularly when a number of different alternative subsets of the balloon array could potentially be in different inflation states to give the same resulting catheter tip and/or tool position and orientation.

As shown in FIG. 2, actuated portion 20 may comprise an axial series of 2 or more (and preferably at least 3) actuatable sub-portions or segments 20', 20", 20'", with the segments optionally being adjacent to each other, or alternatively separated by relatively short (less than 10 diameters) and/or relatively stiff intermediate portions of catheter 12. Each sub-portion or segment may have an associated actuation array, with the arrays working together to provide the desired overall catheter shape and degrees of freedom to the tip or tool. At least 2 of the sub-portions may employ similar articulation components (such as similar balloon arrays, similar structural backbone portions, similar valve systems, and/or similar software). Commonality may include the use of corresponding actuation balloon arrays, but optionally with the characteristics of the individual actuation balloons of the different arrays and the spacing between the locations of the arrays varying for any distal tapering of the catheter body. There may be advantages to the use of differentiated articulation components, for example, with proximal and distal sub portions, 20', 20'" having similar structures that are configured to allow selective lateral bending with at least two degrees of freedom, and intermediate portion 20" being configured to allow variable axial elongation. In many embodiments, however, at least two (and preferably all) segments are substantially continuous and share common components and geometries, with the different segments having separate fluid channels and being separately articulatable but each optionally providing similar movement capabilities.

For those elongate flexible articulated structures described herein that include a plurality of axial segments, the systems will often determine and implement each commanded articulation of a particular segment as a single consistent articulation toward a desired segment shape state that is distributed along that segment. In some exemplary embodiments, the nominal or resting segment shape state may be constrained to a 3 DOF space (such as by continuous combinations of two transverse lateral bending orientations and an axial (elongation) orientation in an X-Y-Z work space). In some of the exemplary embodiments described herein (including at least some of the helical extension/contraction embodiments), lateral bends along a segment may be at least approximately planar when the segment is in or near a design axial length configuration (such as at or near the middle of the axial or Z range of motion), but may exhibit a slight but increasing off-plane twisting curvature as the segment moves away from that design configuration (such as near the proximal and/or distal ends of the axial range of motion).

Figure 3:
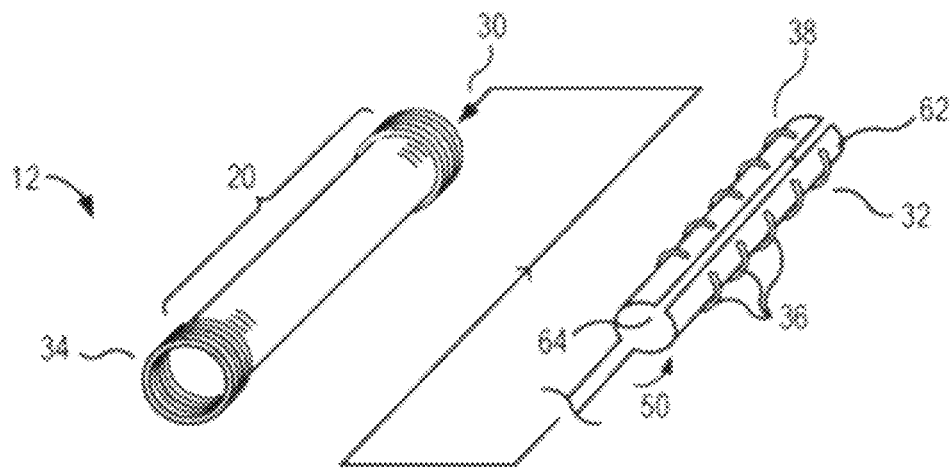
FIG. 3 is a simplified exploded perspective view showing a balloon array that can be formed in a substantially planar configuration and rolled into a cylindrical configuration, and which can be mounted coaxially to a helical coil or other skeleton framework for use in the catheter of the system of FIGS. 1 and 2.
Figure 5:
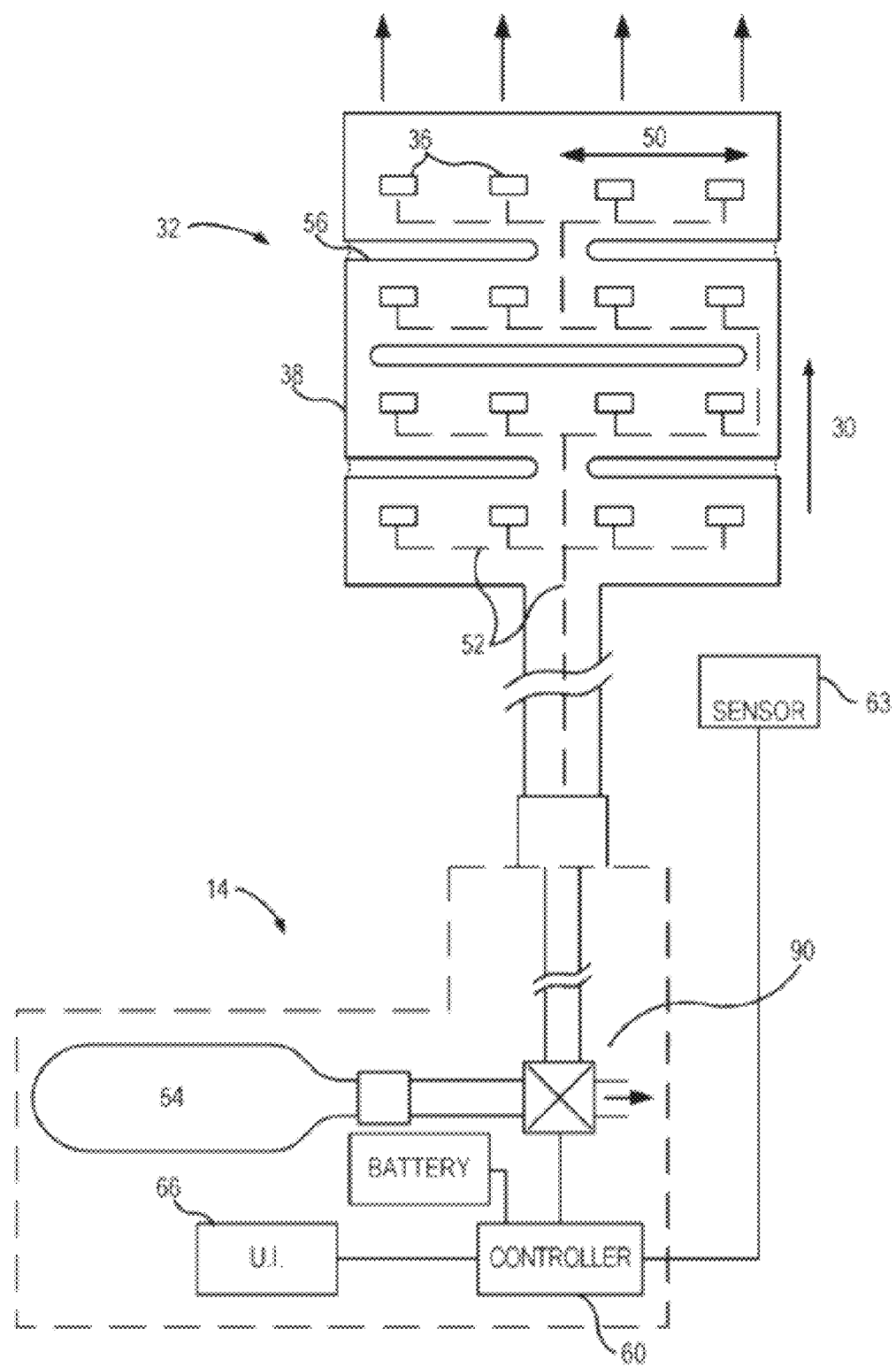
FIG. 5 schematically illustrates components for use in the catheter system of FIG. 1, including the balloon array, inflation fluid source, fluid control system, and processor.

Referring to FIGS. 3 and 5, catheter body 12 of system 10 includes an actuation array structure 32 mounted to a structural skeleton (here in the form of a helical coil 34). Exemplary balloon array 32 includes fluid expandable structures or balloons 36 distributed at balloon locations along a flexible substrate 38 so as to define an M×N array, in which M is an integer number of balloons distributed about a circumference 50 of catheter 12 at a given location along axis 30, and N represents an integer number of axial locations along catheter 12 having actuation balloons. Circumferential and axial spacing of the array element locations will generally be known, and will preferably be regular. This first exemplary actuation array includes a 4×4 array for a total of 16 balloons; alternative arrays may be from 1×2 arrays for a total of 2 balloons to 8×200 arrays for a total of 1600 balloons (or beyond), more typically having from 3×3 to 6×20 arrays.

The balloons of a particular segment or that are mounted to a common substrate may be described as forming an array, with the actuation balloon array structure optionally being used as a sub-array in a multi-segment or opposed articulation system. The combined sub-arrays together may form an array of the overall device, which may also be described simply as an array or optionally an overall or combined array. Exemplary balloon arrays along a segment or sub-portion of articulated portion 20 include 1×8, 1×12, and 1×16 arrays for bending in a single direction (optionally with all of the balloons of the segment in fluid communication with a common inflation lumen so as to be inflated together) and 4×4, 4×8, and 4×12 arrays for X-Y bending (with axially aligned groups of 2-12 balloons coupled with 4 or more common lumens for articulation in the +X, −X, +Y, and −Y orientations). Exemplary arrays may also be in the form of a 3×N balloons arrays with 6 to 48 balloons or more balloons, with the 3 lateral balloon orientations separated by 120 degrees about the catheter axis.

As can be seen in FIGS. 3, 4A, 4B, and 4C, the skeleton will often (though not always) include an axial series of loops 42. When the loops are included in a helical coil 34, the coil may optionally be biased so as to urge adjacent loops 42 of the coil 34 toward each other. Such axially compressive biasing may help urge fluid out and deflate the balloons, and may by applied by other structures (inner and/or outer sheath(s), pull wires, etc.) with or without helical compression. Axial engagement between adjacent loops (directly, or with balloon walls or other material of the array between loops) can also allow compressive axial forces to be transmitted relatively rigidly when the balloons are not inflated. When a particular balloon is fully inflated, axial compression may be transmitted between adjacent loops by the fully inflated balloon wall material and by the fluid within the balloons. Where the balloon walls are non-compliant, the inflated balloons may transfer these forces relatively rigidly, though with some flexing of the balloon wall material adjacent the balloon/skeleton interface. Rigid or semi-rigid interface structures which distribute axial loads across a broader balloon interface region may limit such flexing. Axial tension forces (including those associated with axial bending) may be resisted by the biasing of the skeleton (and/or by other axial compressive structures). Alternative looped skeleton structures may be formed, for example, by cutting hypotube with an axial series of lateral incisions across a portion of the cross-section from one or more lateral orientations, braided metal or polymer elements, or the like. Non-looped skeletons may be formed using a number of alternative known rigid or flexible robotic linkage architectures, including with structures based on known soft robot structures. Suitable materials for coil 34 or other skeleton structures may comprise metals such as stainless steel, spring steel, superelastic or shape-memory alloys such as Nitinol™ alloys, polymers, fiber-reinforced polymers, high-density or ultrahigh-density polymers, or the like.

When loops are included in the skeleton, actuation array 32 can be mounted to the skeleton with at least some of the balloons 36 positioned between two adjacent associated loops 42, such as between the loops of coil 34. Referring now to FIG. 4C, an exemplary deflated balloon 36*i* is located between a proximally adjacent loop 42*i* and a distally adjacent loop 42*ii*, with a first surface region of the balloon engaging a distally oriented surface of proximal loop 34*i*, and a second surface region of the balloon engaging a proximally oriented surface of distal loop 42*ii*. The walls of deflated balloon 36*i* have some thickness, and the proximal and distal surfaces of adjacent loops 42*i* and 42*ii* maintain a non-zero axial deflated offset 41 between the loops. Axial compression forces can be transferred from the loops through the solid balloon walls. Alternative skeletal structures may allow the loops to engage directly against each other so as to have a deflated offset of zero and directly transmit axial compressive force, for example by including balloon receptacles or one or more axial protrusions extending from one or both loops circumferentially or radially beyond the balloon and any adjacent substrate structure. Regardless, full inflation of the balloon will typically increase the separation between the adjacent loops to a larger full inflation offset 41'. The simplified lateral cross-sections of FIGS. 4B, 4C, and 4D schematically show a direct interface engagement between a uniform thickness thin-walled balloon and a round helical coil loop. Such an interface may result in relatively limited area of the balloon wall engaging the coil and associated deformation under axial loading. Alternative balloon-engaging surface shapes along the coils (often including locally increased convex radii, locally flattened surfaces, and/or local concave balloon receptacles) and/or along the coil-engaging surfaces of the balloon (such as by locally thickening the balloon wall to spread the engagement area), and/or providing load-spreading bodies between the balloons and the coils may add axial stiffness. A variety of other modifications to the balloons and balloon/coil interfaces may also be beneficial, including adhesive bonding of the balloons to the adjacent coils, including folds or material so as to inhibit balloon migration, and the like.

Inflation of a balloon can alter the geometry along catheter body 12, for example, by increasing separation between loops of a helical coil so as to bend axis 30 of catheter 12. As can be understood with reference to FIGS. 1B, 1C and 4-4C, selectively inflating an eccentric subset of the balloons can variably alter lateral deflection of the catheter axis. As can be understood with reference to FIGS. 1A, 4, and 4D, inflation of all (or an axisymmetric subset) of the balloons may increase an axial length of the catheter structure. Inflating subsets of the balloons that have a combination of differing lateral orientations and axial positions can provide a broad range of potential locations and orientations of the catheter distal tip 26, and/or of one or more other locations along the catheter body (such as where a tool is mounted).

Some or all of the material of substrate 38 included in actuation array 32 will often be relatively inelastic. It may, however, be desirable to allow the skeleton and overall catheter to flex and/or elongate axially with inflation of the balloons or under environmental forces. Hence, array 32 may have cutouts 56 so as to allow the balloon array to move axially with the skeleton during bending and elongation. The array structure could alternatively (or in addition) be configured for such articulation by having a serpentine configuration or a helical coiled configuration. Balloons 36 of array 32 may include non-compliant balloon wall materials, with the balloon wall materials optionally being formed integrally from material of the substrate or separately. Note that elastic layers or other structures may be included in the substrate for use in valves and the like, and that some alternative balloons may include elastic and/or semi-compliant materials.

Figure 4A:
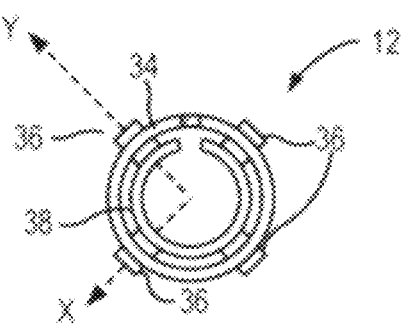
FIGS. 4A and 4B are a simplified cross-section and a simplified transverse cross-section, respectively, of an articulatable catheter for use in the system of FIG. 1, shown here with the balloons of the array in an uninflated, small axial profile configuration and between loops of the coil.
Figure 4B:
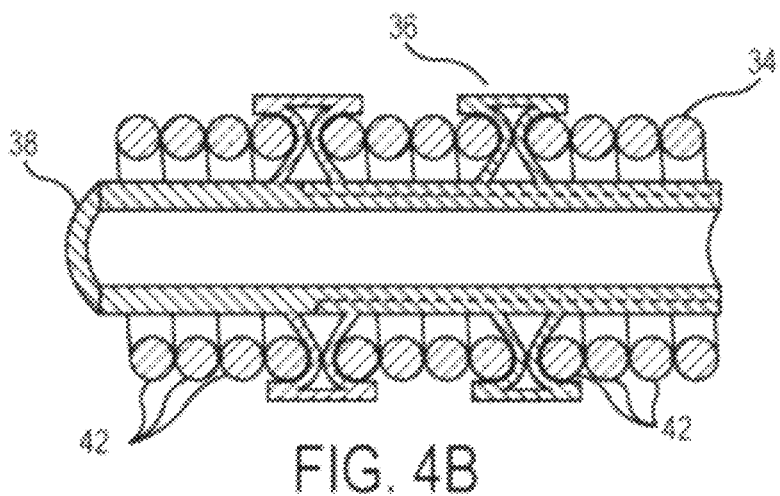
Figure 4C:
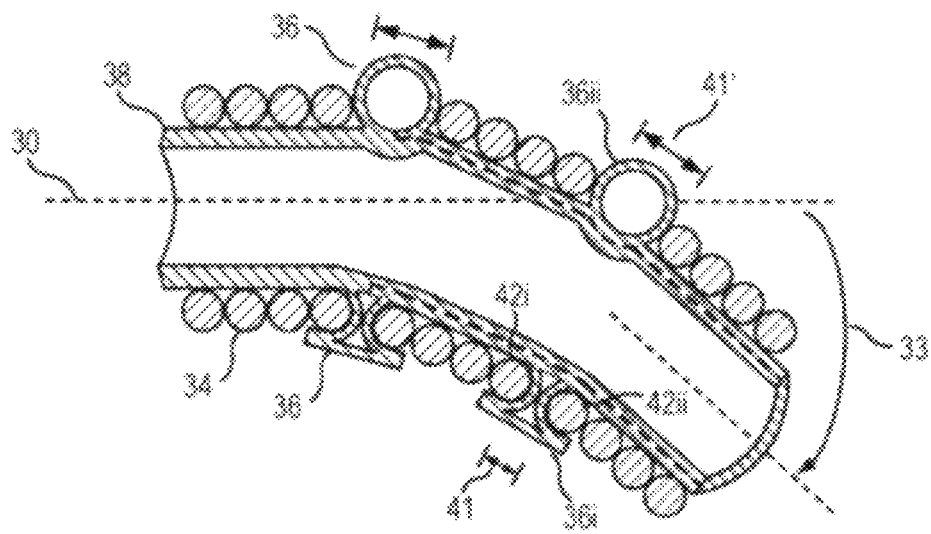
FIG. 4C is a simplified transverse cross-section of the articulatable catheter of FIGS. 4A and 4B, with a plurality of axially aligned balloons along one side of the articulatable region of the catheter inflated so that the catheter is in a laterally deflected state.
Figure 4D:
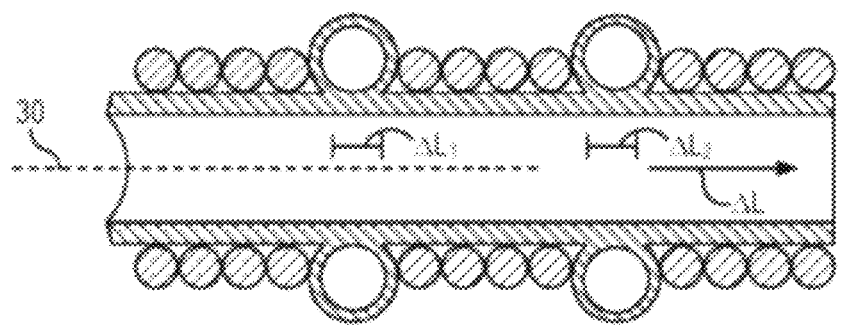
FIG. 4D is a simplified transverse cross-section of the articulatable catheter of FIG. 4, with a plurality of laterally opposed balloons inflated so that the catheter is in an axially elongated state.

Referring to FIGS. 3, 4A, and 5, substrate 38 of array 32 is laterally flexible so that the array can be rolled or otherwise assume a cylindrical configuration when in use. The cylindrical array may be coaxially mounted to (such as being inserted into or radially outwardly surrounding) the helical coil 34 or other structural backbone of the catheter. The cylindrical configuration of the array will generally have a diameter that is equal to or less than an outer diameter of the catheter. The opposed lateral edges of substrate 38 may be separated by a gap as shown, may contact each other, or may overlap. Contacting or overlapping edges may be affixed together (optionally so as to help seal the catheter against radial fluid flow) or may accommodate relative motion (so as to facilitate axial flexing). In some embodiments, lateral rolling or flexing of the substrate to form the cylindrical configuration may be uniform (so as to provide a continuous lateral curve along the major surfaces), while in other embodiments intermittent axial bend regions of the substrate may be separated by axially elongate relatively flat regions of the substrate so that a cylindrical shape is approximated by a prism-like arrangement (optionally so as to limit bending of the substrate along balloons, valves, or other array components). It will often (though not always) be advantageous to form and/or assemble one or more components of the array structure in a flat, substantially planar.

As can be understood with reference to FIGS. 5-5C, substrate 38 of array 32 may include one or more layers 70, 72, 74 . . . of flexible substrate material. The substrate layers may comprise known flexible and/or rigid microfluidic substrate materials, such as polydimethylsiloxane (PDMS), polyimide (PI), polyethylene (PE) and other polyolefins, polystyrene (PS), polyethylene terephthalate (PET), polypropylene (PP), polycarbonate (PC), nanocomposite polymer materials, glass, silicon, cyclic olefin copolymer (COC), polymethyl methacrylate (PMMA), polyetheretherketone (PEEK), polyester, polyurethane (PU), and/or the like. These and still further known materials may be included in other components of actuation array 32, including known polymers for use in balloons (which will often include PET, PI, PE, polyether block amide (PEBA) polymers such as PEBAX™ polymers, nylons, urethanes, polyvinyl chloride (PVC), thermoplastics, and/or the like for non-compliant balloons; or silicone, polyurethane, semi-elastic nylons or other polymers, latex, and/or the like for compliant or semi-compliant balloons). Additional polymers than may be included in the substrate assembly may include valve actuation elements (optionally including shape memory alloy structures or foils; phase-change actuator materials such as paraffin or other wax, electrical field sensitive hydrogels, bimetallic actuators, piezoelectric structures, dielectric elastomer actuator (DEA) materials, or the like). Hence, while some embodiments may employ homogenous materials for actuation array 32, many arrays and substrate may instead be heterogeneous.

The structures of balloons 36 as included in actuation array 32 may be formed of material integral with other components of the array, or may be formed separately and attached to the array. For example, as shown in FIGS. 5B and 5C, balloons 36 may be formed from or attached to a first sheet 74 of substrate material that can be bonded or otherwise affixed to another substrate layer 72 or layers. The material of the balloon layer 74 may optionally cover portions of the channels directly, or may be aligned with apertures 78 that open through an intermediate substrate layer surface between the channels and the balloons. Apertures 78 may allow fluid communication between each balloon and at least one associated channel 52. Alternative methods for fabricating individual balloons are well known, and the formed balloons may be affixed to the substrate 38 by adhesive bonding. Balloon shapes may comprise relatively simple cylinders or may be somewhat tailored to taper to follow an expanded offset between loops of a coil, to curve with the cylindrical substrate and/or to engage interface surfaces of the skeleton over a broader surface area and thereby distribute actuation and environmental loads. Effective diameters of the balloons in the array may range from about 0.003 mm to as much as about 2 cm (or more), more typically being in a range from about 0.3 mm to about 2 mm or 5 mm, with the balloon lengths often being from about 2 to about 15 times the diameter. Typical balloon wall thicknesses may range from about 0.0002 mm to about 0.004 mm (with some balloon wall thicknesses being between 0.0002 mm and 0.12 mm), and full inflation pressures in the balloons may be from about 0.2 to about 40 atm, more typically being in a range from about 0.4 to about 30 atm, and in some embodiments being in a range from about 10 to about 30 atm, with high-pressure embodiments operating at pressures in a range as high as 20-45 atm and optionally having burst pressures of over 50 atm.

Referring now to FIG. 5, balloons 36 will generally be inflated using a fluid supply system that includes a fluid source 54 (shown here as a pressurized single-use cartridge) and one or more valves 90. At least some of the valves 90 may be incorporated into the balloon array substrate, with the valves optionally being actuated using circuitry printed on one or more layers of substrate 38. With or without substrate-mounted valves that can be used within a patient body, at least some of the valves may be mounted to housing 14, or otherwise coupled to the proximal end of catheter 12. Valves 90 will preferably be coupled to channels 52 so as to allow the fluid system to selectively inflate any of a plurality of alternative individual balloons or subsets of balloons 36 included in actuation array 32, under the direction of a processor 60. Hence, processor 60 will often be coupled to valves 90 via conductors, the conductors here optionally including flex circuit traces on substrate 38.

Referring still to FIG. 5, fluid source 54 may optionally comprise a separate fluid reservoir and a pump for pressurizing fluid from the reservoir, but will often include a simple tank or cartridge containing a pressurized fluid, the fluid optionally being a gas or a gas-liquid mixture. The cartridge will often maintain the fluid at a supply pressure at or above a full inflation pressure range of balloons 36, with the cartridge optionally being gently heated by a resistive heater or the like (not shown) in housing 14 so as to maintain the supply pressure within a desired range in the cartridge during use. Supply pressures will typically exceed balloon inflation pressures sufficiently to provide balloon inflation times within a target threshold given the pressure loss through channels 52 and valves 90, with typical supply pressures being between 10 and 210 atm, and more typically being between 20 and 60 atm. Suitable fluids may include known medical pressurized gases such as carbon dioxide, nitrogen, oxygen, nitrous oxide, air, known industrial and cryogenic gasses such as helium and/or other inert or noble gasses, refrigerant gases including fluorocarbons, and the like. Note that the pressurized fluid in the canister can be directed via channels 52 into balloons 36 for inflation, or the fluid from the canister (often at least partially a gas) may alternatively be used to pressurize a fluid reservoir (often containing or comprising a benign biocompatible liquid such as water or saline) so that the balloon inflation fluid is different than that contained in the cartridge. Where a pressurized liquid or gas/liquid mixture flows distally along the catheter body, enthalpy of vaporization of the liquid in or adjacent to channels 52, balloons 36, or other tissue treatment tools carried on the catheter body (such as a tissue dilation balloon, cryogenic treatment surface, or tissue electrode) may be used to therapeutically cool tissue. In other embodiments, despite the use of fluids which are used as refrigerants within the body, no therapeutic cooling may be provided. The cartridge may optionally be refillable, but will often instead have a frangible seal so as to inhibit or limit re-use.

As the individual balloons may have inflated volumes that are quite small, cartridges that are suitable for including in a hand-held housing can allow more than a hundred, optionally being more than a thousand, and in many cases more than ten thousand or even a hundred thousand individual balloon inflations, despite the cartridge containing less than 10 ounces of fluid, often less than 5 ounces, in most cases less than 3 ounces, and ideally less than 1 ounce. Note also that a number of alternative fluid sources may be used instead of or with a cartridge, including one or more positive displacement pumps (optionally such as simple syringe pumps), a peristaltic or rotary pump, any of a variety of microfluidic pressure sources (such as wax or other phase-change devices actuated by electrical or light energy and/or integrated into substrate 38), or the like. Some embodiments may employ a series of dedicated syringe or other positive displacement pumps coupled with at least some of the balloons by channels of the substrate, and/or by flexible tubing.

Referring still to FIG. 5, processor 60 can facilitate inflation of an appropriate subset of balloons 36 of actuation array 32 so as to produce a desired articulation. Such processor-derived articulation can significantly enhance effective operative coupling of the input 18 to the actuated portion 20 of catheter body 12, making it much easier for the user to generate a desired movement in a desired direction or to assume a desired shape. Suitable correlations between input commands and output movements have been well developed for teleoperated systems with rigid driven linkages. For the elongate flexible catheters and other bodies used in the systems described herein, it will often be advantageous for the processor to select a subset of balloons for inflation based on a movement command entered into a user interface 66 (and particularly input 18 of user interface 66), and on a spatial relationship between actuated portion 20 of catheter 12 and one or more component of the user interface. A number of differing correlations may be helpful, including orientational correlation, displacement correlation, and the like. Along with an input, user interface 66 may include a display showing actuated portion 20 of catheter body 12, and sensor 63 may provide signals to processor 60 regarding the orientation and/or location of proximal base 21. Where the relationship between the input, display, and sensor are known (such as when they are all mounted to proximal housing 14 or some other common base), these signals may allow derivation of a transformation between a user interface coordinate system and a base coordinate system of actuated portion 20. Alternative systems may sense or otherwise identify the relationships between the sensor coordinate system, the display coordinate system, and/or the input coordinate system so that movements of the input result in catheter movement, as shown in the display. Where the sensor comprises an image processor coupled to a remote imaging system (such as a fluoroscopy, MRI, or ultrasound system), high-contrast marker systems can be included in proximal base 21 to facilitate unambiguous determination of the base position and orientation. A battery or other power source (such as a fuel cell or the like) may be included in housing 14 and coupled to processor 60, with the housing and catheter optionally being used as a handheld unit free of any mechanical tether during at least a portion of the procedure. Nonetheless, it should be noted that processor 60 and/or sensor 63 may be wirelessly coupled or even tethered together (and/or to other components such as a separate display of user interface 66, an external power supply or fluid source, or the like).

Regarding processor 60, sensor 63, user interface 66, and the other data processing components of system 10, it should be understood that the specific data processing architectures described herein are merely examples, and that a variety of alternatives, adaptations, and embodiments may be employed. The processor, sensor, and user interface will, taken together, typically include both data processing hardware and software, with the hardware including an input (such as a joystick or the like that is movable relative to housing 14 or some other input base in at least 2 dimensions), an output (such as a medical image display screen), an image-acquisition device or other sensor, and one or more processor. These components are included in a processor system capable of performing the image processing, rigid-body transformations, kinematic analysis, and matrix processing functionality described herein, along with the appropriate connectors, conductors, wireless telemetry, and the like. The processing capabilities may be centralized in a single processor board, or may be distributed among the various components so that smaller volumes of higher-level data can be transmitted. The processor(s) will often include one or more memory or storage media, and the functionality used to perform the methods described herein will often include software or firmware embodied therein. The software will typically comprise machine-readable programming code or instructions embodied in non-volatile media, and may be arranged in a wide variety of alternative code architectures, varying from a single monolithic code running on a single processor to a large number of specialized subroutines being run in parallel on a number of separate processor sub-units.

Figure 6:
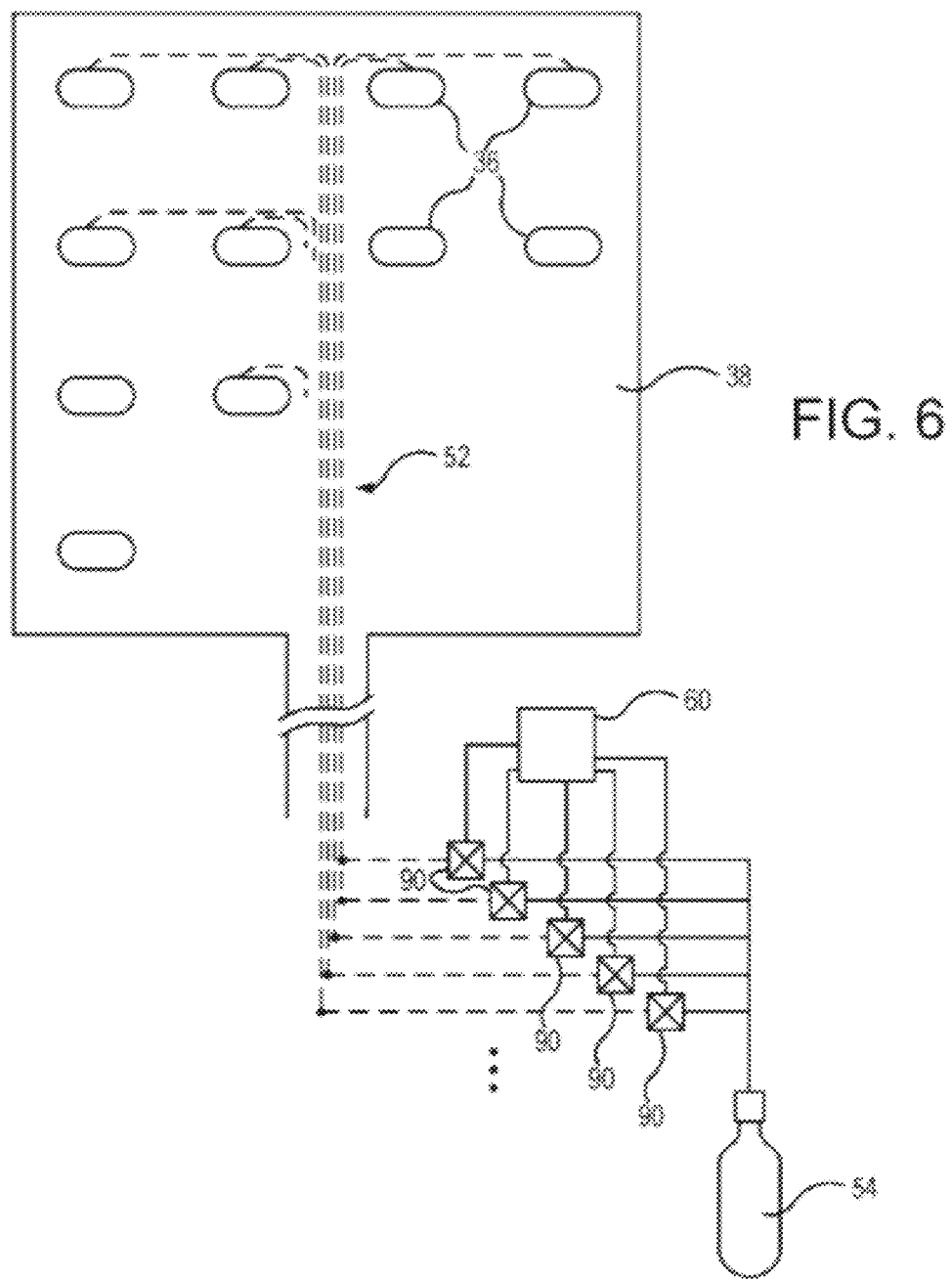
FIG. 6 is a simplified schematic of an alternative balloon array and fluid control system, in which a plurality of valves coupled with the proximal end of the catheter can be used to direct fluid to any of a plurality of channels of the array and thereby selectably determine a subset of balloons to be expanded.

Referring now to FIG. 6, an alternative actuation array and fluid supply system are shown schematically. As in the above embodiment, balloons 36 are affixed along a major surface of substrate 38, optionally prior to rolling the substrate and mounting of the actuation array to the skeleton of the catheter body. In this embodiment, each balloon has an associated dedicated channel 52 of substrate 38, and also an associated valve 90. Processor 60 is coupled with valves 90, and by actuating a desired subset of the valves the associated subset of balloons can be inflated or deflated. In some embodiments, each valve can be associated with more than one balloon 36, so that (for example), opening of a single valve might inflate a plurality (optionally 2, 3, 4, 8, 12, or some other desired number) of balloons, such as laterally opposed balloons so as to elongate the distal portion of the catheter. In these or other embodiments, a plurality of balloons (2, 3, 4, 5, 8, 12, or another desired number) on one lateral side of the catheter could be in fluid communication with a single associated valve 90 via a common channel or multiple channels so that opening of the valve inflates the balloons and causes a multi-balloon and multi-increment bend in the axis of the catheter. Still further variations are possible. For example, in some embodiments, channels 52 may be formed at least in-part by flexible tubes affixed within an open or closed channel of substrate 38, or glued along a surface of the substrate. The tubes may comprise polymers (such as polyimide, PET, nylon, or the like), fused silica, metal, or other materials, and suitable tubing materials may be commercially available from Polymicro Technologies of Arizona, or from a variety of alternative suppliers. The channels coupled to the proximal end of the actuatable body may be assembled using stacked fluidic plates, with valves coupled to some or all of the plates. Suitable electrically actuated microvalues are commercially available from a number of suppliers. Optional embodiments of fluid supply systems for all balloon arrays described herein may have all values mounted to housing 14 or some other structure coupled to and/or proximal of) the proximal end of the elongate flexible body. Advantageously, accurately formed channels 52 (having sufficiently tight tolerance channel widths, depths, lengths, and/or bends or other features) may be fabricated using microfluidic techniques, and may be assembled with the substrate structure, so as to meter flow of the inflation fluid into and out of the balloons of all of the actuation arrays described herein.

Reviewing components of an exemplary helical frame contraction/expansion articulation system, FIGS. 7A-7E illustrate actuation balloon array components and their use in a helical balloon assembly.

Figure 7A:
Figure 7B:
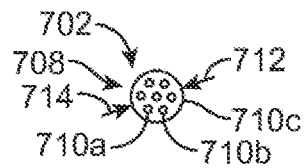

Referring now to FIGS. 7A and 7B, an exemplary multi-lumen conduit or balloon assembly core shaft is shown. Core 702 has a proximal end 704 and a distal end 706 with a multi-lumen body 708 extending therebetween. A plurality of lumens 710a, 710b, 710c, . . . extend between the proximal and distal ends. The number of lumens included in a single core 702 may vary between 3 and 30, with exemplary embodiments have 3, 7 (of which one is a central lumen), 10 (including 1 central), 13 (including 1 central), 17 (one being central), or the like. The multi-lumen core will often be round but may alternatively have an elliptical or other elongate cross-section as described above. When round, core 702 may have a diameter 712 in a range from about 0.010" to about 1", more typically being in a range from about 0.020" to about 0.250", and ideally being in a range from about 0.025" to about 0.100" for use in catheters. Each lumen will typically have a diameter 714 in a range from about 0.0005" to about 0.05", more preferably having a diameter in a range from about 0.001" to about 0.020", and ideally having a diameter in a range from about 0.0015" to about 0.010". The core shafts will typically comprise extruded polymer such as a nylon, urethane, PEBAX, PEEK, PET, other polymers identified above, or the like, and the extrusion will often provide a wall thickness surrounding each lumen of more than about 0.0015", often being about 0.003" or more. The exemplary extruded core shown has an OD of about 0.0276"", and 7 lumens of about 0.004" each, with each lumen surrounded by at least 0.004" of the extruded nylon core material.

Referring still to FIGS. 7A and 7B, the lumens of core 702 may have radial balloon/lumen ports 716a, 716b, 716c, . . . , with each port comprising one or more holes formed through the wall of core 702 and into an associated lumen 710a, 710b, 710c, . . . respectively. The ports are here shown as a group of 5 holes, but may be formed using 1 or more holes, with the holes typically being round but optionally being axially elongate and/or shaped so as to reduce pressure drop of fluid flow therethrough. In other embodiments (and particularly those having a plurality of balloons supplied with inflation fluid by a single lumen), having a significant pressure drop between the lumen and the balloon may help even the inflation state of balloons, so that a total cross section of each port may optionally be smaller than a cross-section of the lumen (and/or by limiting the ports to one or two round lumens). Typical ports may be formed using 1 to 10 holes having diameters that are between 10% of a diameter of the associated lumen and 150% of the diameter of the lumen, often being from 25% to 100%, and in many cases having diameters of between 0.001" and 0.050". Where more than one hole is included in a port they will generally be grouped together within a span that is shorter than a length of the balloons, as each port will be contained within an associated balloon. Spacing between the ports will correspond to a spacing between balloons to facilitate sealing of each balloon from the axially adjacent balloons.

Regarding which lumens open to which ports, the ports along a distal portion of the core shaft will often be formed in sets, with each set being configured to provide fluid flow to and from an associated set of balloons that will be distributed along the loops of the core (once the core is bent to a helical configuration) for a particular articulated segment of the articulated flexible body. When the number of lumens in the core is sufficient, there will often be separate sets of ports for different segments of the articulated device. The ports of each set will often form a periodic pattern along the axis of the multi-lumen core 702, so that the ports provide fluid communication into M different lumens (M being the number of different balloon orientations that are to be distributed about the articulated device axis, often being 3 or 4, i.e., lumen 710a, lumen 710b, and lumen 710c) and the pattern repeating N times (N often being the number of contraction balloons along each orientation of a segment). Hence, the multi-lumen core conduit can function as a substrate that supports the balloons, and that defines the balloon array locations and associated fluid supply networks described above.

Figure 7C:
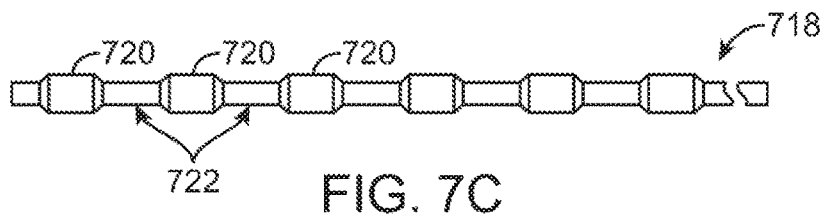
Figure 7D:

Referring now to FIGS. 7C and 7D, a continuous tube of flexible balloon wall material 718 may be formed by periodically varying a diameter of tube wall material to form a series of balloon shapes 720 separated by smaller profile sealing zones 722. Balloon tube 718 may include between about 9 and about 290 regularly spaced balloon shapes 720, with the sealing zones typically having an inner diameter that is about equal to the outer diameters of the multi-lumen helical core shafts 702 described above. In some embodiments, the inner diameters of the sealing zones may be significantly larger than the outer diameters of the associated cores when the balloon tube is formed, and the diameters of the sealing zones may be decreased (such as by heat shrinking or axially pull-forming) before or during assembly of the balloon tube and core shaft. The sealing zone may have a length of between about 0.025" and about 0.500", often being between about 0.050" and about 0.250". Decreasing the length of the sealing zone allows the length of the balloon to be increased for a given catheter size so as to provide larger balloon/frame engagement interfaces (and thus greater articulation forces), while longer sealing zones may facilitate assembly and sealing between balloons so as to avoid cross-talk between articulation channels.

Referring still to FIGS. 7C and 7D, the balloon shapes 720 of the balloon tube 718 may have diameters that are larger than the diameters of the sealing zones by between about 10% and about 200%, more typically being larger by an amount in a range from about 20% to about 120%, and often being from about 40% to about 75%. The thickness of balloon tube 718 will often vary axially with the varying local diameter of the tube, the locally large diameter portions forming the balloon shapes optionally being in a range from about 0.00008' (or about 2 microns) to about 0.005", typically being from about 0.001" and about 0.003". Balloon tube 718 may initially be formed with a constant diameter and thickness, and the diameter may be locally expanded (by blow forming, by vacuum forming, by a combination of both blow forming and vacuum forming, or by otherwise processing the tube material along the balloon shapes 720), and/or the diameter of the balloon tube may be locally decreased (by heat shrinking, by axial pull-forming, by a combination of both heat shrinking and pull forming, or by otherwise processing the tube material along the sealing zones), with the tube material often being processed so as to both locally expand the diameter along the desired balloon shapes and to locally contract the diameter along the sealing zones. It should be noted that while a single continuous balloon tube is shown, a plurality of balloon tubes (each having a plurality (or in some cases, at least one) balloon shape) can be sealingly mounted onto a single core. Regardless, the sealing zones will often have a material thickness that is greater than that of the balloon shapes.

The balloon shapes 720 of the balloon tube 718 may each have a relatively simple cylindrical center section prior to assembly as shown. The tapers between the balloon center sections and the sealing zones can take any of a variety of shapes. The tapers may, for example, be roughly conical, rounded, or squared, and will preferably be relatively short so as to allow greater balloon/frame engagement for a given landing zone length. More complex embodiments may also be provided, including forming the balloon shapes with curved cylindrical center sections, optionally while corrugating or undulating the surfaces of the tapers so that the balloon tube overall remains relatively straight. The lengths of each center section is typically sufficient to define an arc-angle of from 5 to 180 degrees about the axis of the desired balloon assembly helix, more typically being from about 10 to about 50 degrees, the lengths of the center sections often being in a range from about 0.010" to about 0.400" for medical applications, more typically being from about 0.020" to about 0.150", and many times being in a range from about 0.025" to about 0.100". The exemplary balloon shapes may have an outer diameter of about 0.051" over a total balloon length (including the tapers) of about 0.059"

Figure 7E:
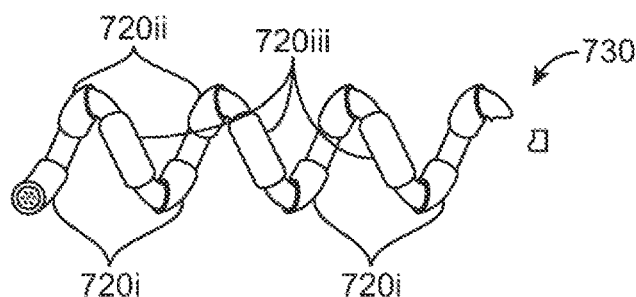
Figures 1, 7E:
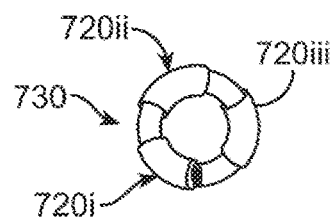
Figures 2, 7E:
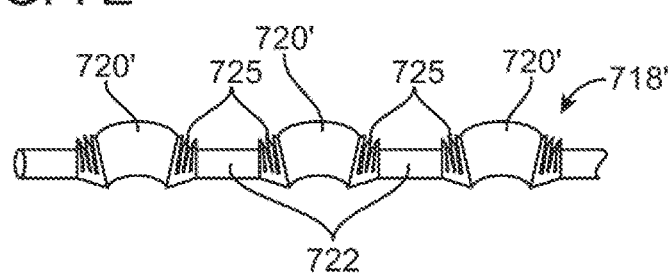

As can be understood with reference to FIGS. 7C, 7D, 7E, and 7E-1, balloon tube 718 may be sealingly affixed to core 702, and the core/balloon tube assembly may then be formed into a desired helical shape. The balloon tube may be sealed over the helical core using adhesive (such as any of those described above, often including UV-cured adhesives) thermal bonding, laser bonding, die bonding, and/or the like. Sealing of the balloons may also benefit from a compression structure disposed over the balloon material to help maintain tube/core engagement when the balloons are inflated. Suitable compression structures or techniques may include short sections of heat-shrink materials (such as PET) shrunk onto the sealing zones, high-strength filament windings wrapped circumferentially around the sealing zones and adhesively bonded, swaging of metallic ring structures similar to marker bands over the sealing zones, small bore crimp clamps over the sealing zones, heat-shrinking and/or pull forming the balloon tube onto the core, or the like. Any two or more of these may also be combined, for example, with the balloon tube being adhesively bonded to the core tube by injecting adhesive into the balloon tube around the sealing zone, heat shrinking the balloon tube and a surrounding PET sleeve over the sealing zone, and then swaging a metallic marker band over the sealing PET sleeve (so that the sleeve provides strain relief). Regardless, ports 716 will preferably be disposed within corresponding balloon shapes 720 and will remain open after the balloon/core assembly 730 is sealed together in the straight configuration shown in FIG. 7D. Shape setting of the balloon/core assembly from the straight configuration to the helically curved configuration of FIG. 7E can be performed by wrapping the assembly around and/or within a mandrel and heating the wrapped assembly. Helical channels may be included in the mandrel, which may also have discrete balloon receptacles or features to help ensure alignment of sets of balloons along the desired lateral balloon axes. Regardless, shape setting of the core/balloon assembly can help set the M different lateral orientations of the balloons, so that the balloons of each set 720*i*, 720*ii*, 720*iii* are aligned, as seen in FIG. 7E-1. As noted elsewhere, due to some slight changes in the geometry of the coiled assembly during axial elongation and the like, there may be some slight circumferential offset between balloons of the same lateral bending orientation when the articulated structure and/or its components are in some configurations, including when at rest.

Referring to FIG. 7E-2, an alternative balloon tube 718' has a plurality of pre-curved balloon shapes 720' coupled together by sealing zones 722 to facilitate forming and/or keeping the balloon/core assembly in a helical configuration. The overall configuration of alternative balloon tube 718' is straight, and it may be beneficial to provide asymmetric corrugated transitions 725 between pre-curved balloon shapes 720' and sealing zones 722. Corrugated transitions 725 may have a form analogous to that of a corrugated straw along at least an outer radial portion of the helix, and the balloon shapes may optionally have corrugations along this outer portion instead of or in addition to the pre-curvature shown schematically here. The balloon shapes, transitions, and sealing zones may be formed by blow molding within machined or printed tooling using medical balloon blowing techniques, by blow molding with the moving tooling of a corrugation system, or the like.

Referring now to FIGS. 8A-9G, an exemplary valve deployment system 1100 includes a balloon drive system 1102 to move a sheath 1104 axially from over a self-expanding prosthetic heart valve 1106, and optionally to recapture the valve prior to complete deployment. Deployment system 1100 generally has a proximal end 1108 and a distal end 1110, with an elongate flexible catheter body 1112 extending much of the axial length of the catheter (not shown in some drawings).

Figure 9A:
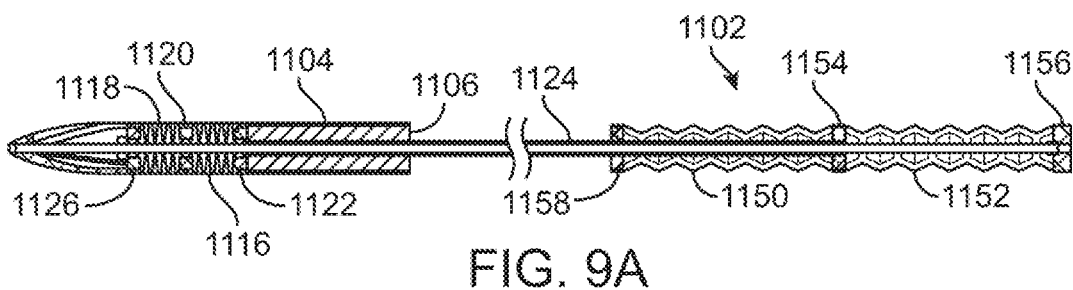
FIGS. 9A-9G are cross-sectional illustrations of the fluid-driven sheath actuation system of FIGS. 8A-8G showing how inflation of the balloon actuators can generate forces within a patient body so as to move the sheath over the self-expanding heart valve to partially deploy the valve, recapture the valve, and fully deploy the valve.
Figure 9B:
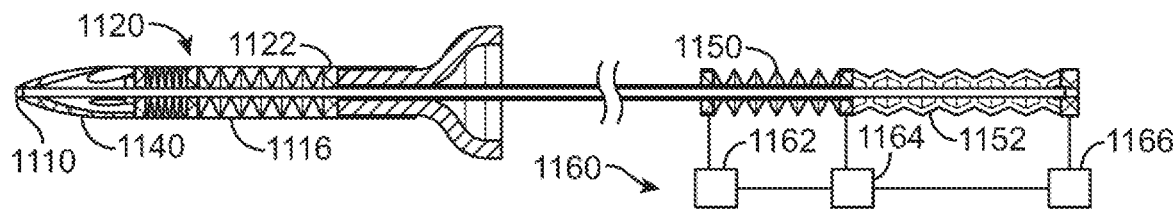
Figure 9C:
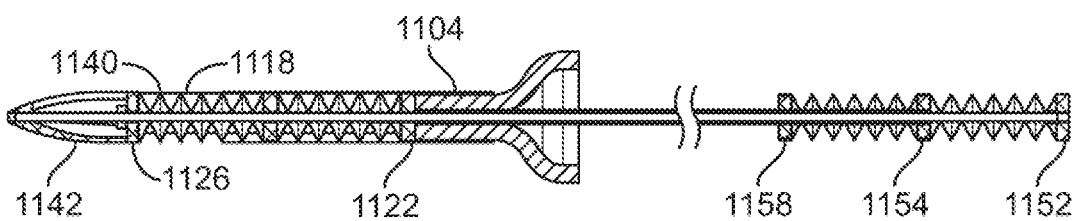
Figure 9D:
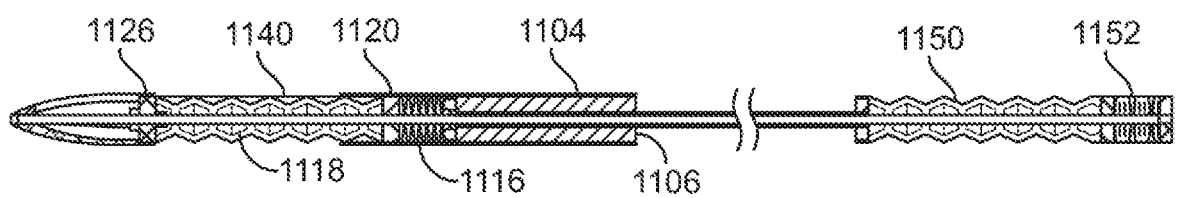
Figure 9E:
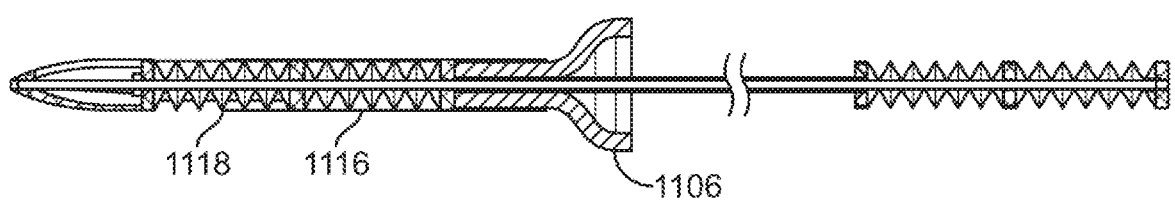
Figure 9F:
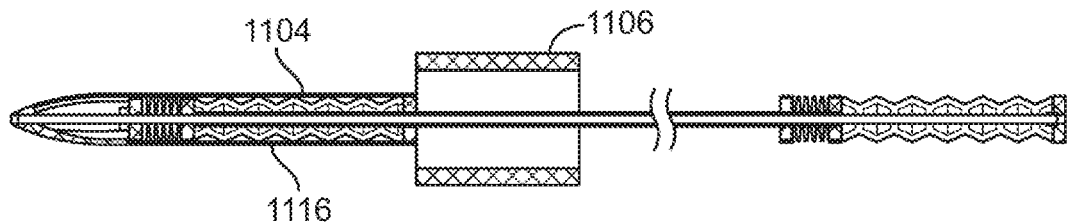
Figure 9G:
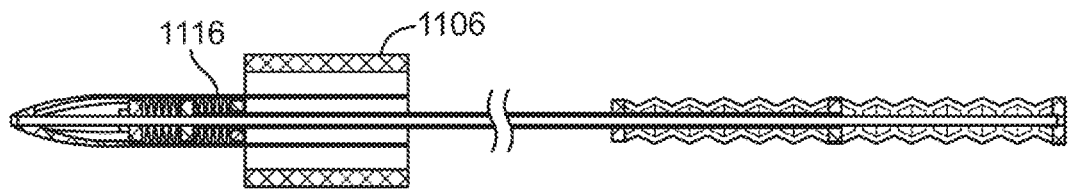
Figure 10A:
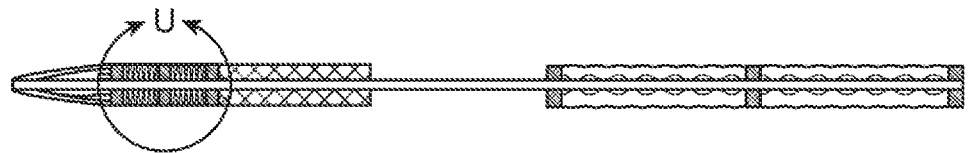
FIGS. 10A-10D are cross-sectional illustrations showing details of the structure and the fluid flow paths of the fluid-driven sheath actuation system of FIGS. 8A-8G.
Figure 10B:
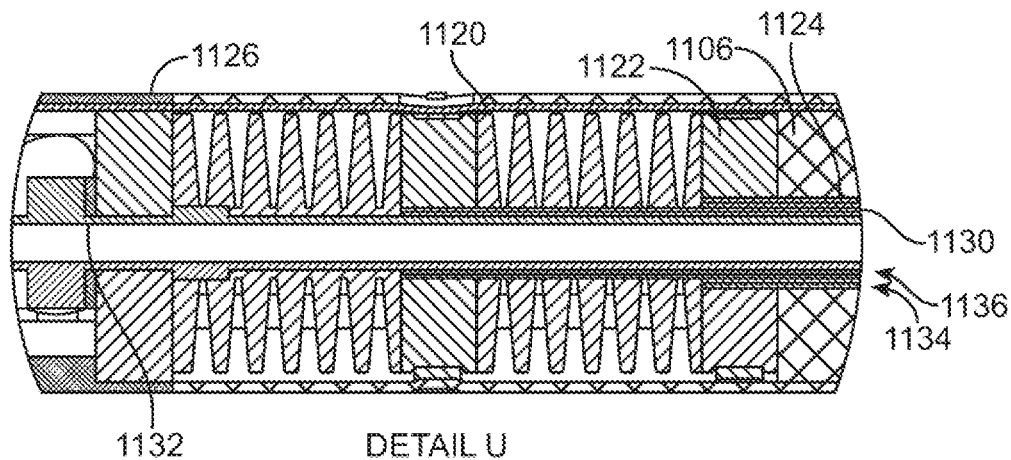
Figure 10C:
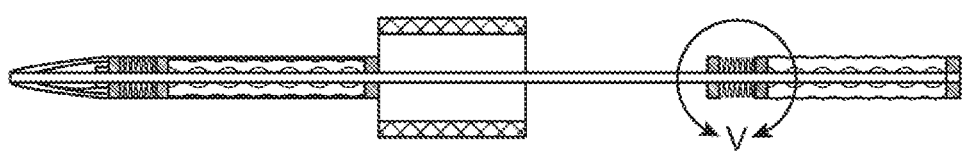
Figure 10D:
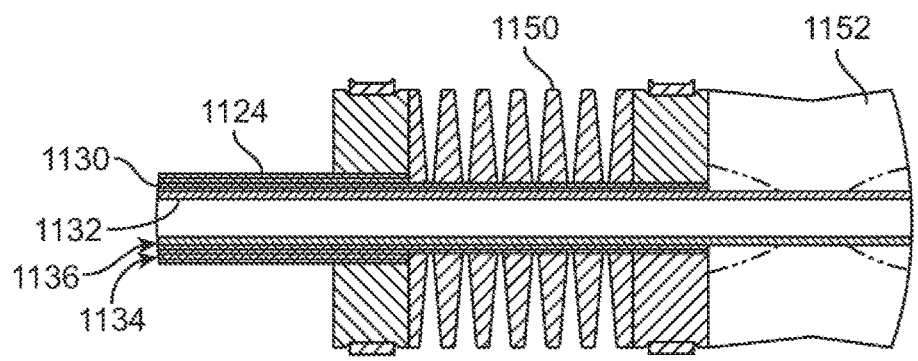
Figure 11A:
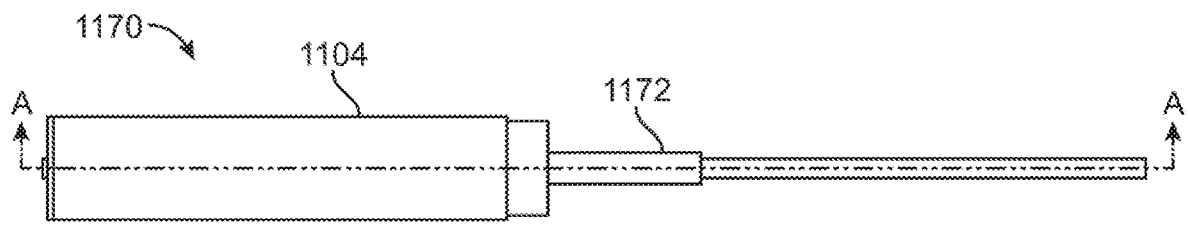
FIGS. 11A-11D are a side view, a cross-section, and two details views showing an alternative distal portion of a valve delivery system having a fluid-driven sheath driven by pressure contained between inner and outer balloons.
Figure 11B:
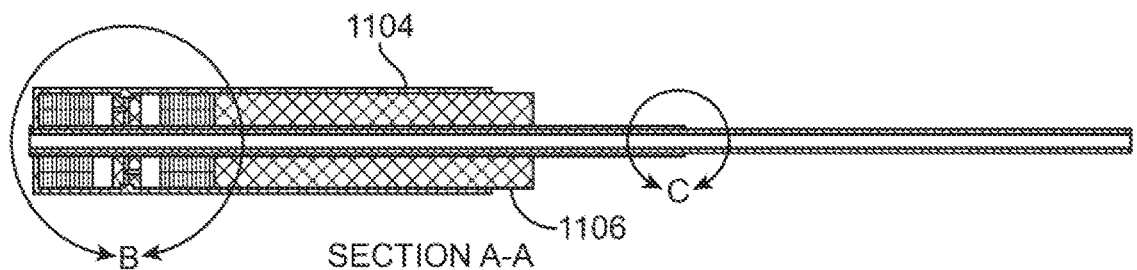
Figure 11C:
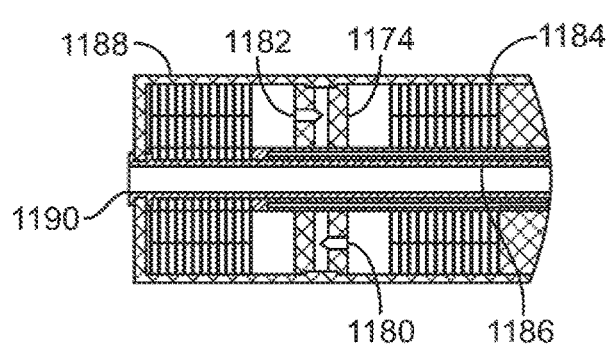
Figure 11D:
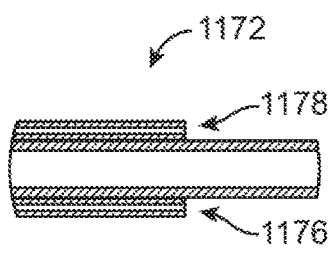

As shown in FIGS. 8A and 9A, when deployment system 1100 is configured to be inserted distally into the patient a receptacle 1114 of catheter body 1112 receives valve 1106. Sheath 1104 radially restrains valve 1106, and the valve can impose radial forces against the sheath that are sufficient to induce significant friction, so that many pounds of axial force will be applied to move the sheath axially from over the valve. Axially oriented surfaces of the catheter body can engage and maintain an axial position of the valve during articulation of the sheath. Sutures or other tension members, valve-engaging features radially protruding from the receptacle within the valve, or the like may be included to inhibit axial movement of the valve relative to the receptacle prior to complete release of the valve from the catheter system. As seen in FIGS. 8A, 9A, together with the detail view of FIG. 10B, distal of the receptacle, a proximal flange 1122 is affixed to a catheter shaft 1124 of the catheter body and forms the proximal end of a deployment balloon 1116, with a proximal surface of the proximal flange forming the distal border of the valve receptacle. Deployment balloon 1116 and a recapture balloon 1118 are separated by an intermediate flange 1120, which is affixed to an intermediate shaft 1130 that can slide axially in a lumen of the catheter shaft. A distal flange 1126 forms the distal end of recapture balloon 1118, and is affixed to an inner shaft 1132 that can slide axially in a lumen of the intermediate shaft. An annular deployment balloon inflation fluid flow path 1134 is bordered by the lumen of catheter shaft 1124 and the outer surface of the intermediate shaft, and an annular recapture balloon inflation fluid flow path 1136 is bordered by the lumen of the intermediate shaft and the outer surface of the inner shaft 1132.

Referring now to FIGS. 8A, 8B, 9A, 9B, and 10B, distal end 1110 may be advanced over a guidewire into a patient, often via femoral access to a right atrium of a heart. The deployment system may then be advanced transseptally through a left atrium so that valve 1106 is aligned with the native mitral valve tissue of the heart (ideally using an articulation balloon array system as described above, but alternatively using a pull-wire, magnetic, or other catheter control system). While valve 1106 is held in position by the catheter structure proximal of the receptacle, sheath 1104 can be moved distally from over the receptacle by transmitting inflation fluid along deployment fluid path 1134, the inflation fluid preferably comprising a non-compressible fluid, typically a liquid such as water, saline, or other biocompatible hydraulic fluid. The inflation fluid axially expands deployment balloon 1116 from an uninflated configuration to a partially inflated configuration, with the deployment balloon preferably having an axial series of laterally opposed folds in the uninflated configuration. The fluid pressure in deployment balloon 1116 drives intermediate flange 1120 (and intermediate shaft 1130 on which the intermediate flange is mounted) distally, pushing distal end 1110 distally from the valve. As sheath 1104 is axially affixed to intermediate flange 1120 (in the exemplary embodiment, via a swage and/or adhesive bonding), this advances the sheath distally from over the prosthetic valve (the laterally stiff sheath advancing in an antegrade direction into the left ventricle, away from the bends of the catheter that maintain prosthetic valve alignment) and allows a proximal portion of the valve to radially expand into engagement with the surrounding native tissue of the mitral valve annulus. Sheath advancement forces can be significant (often being 1 lbf or more, generally being 3 or even 5 lbf or more, and in many cases being 10 or even 15 lbf or more) are generated by fluid pressures in deployment balloon 1116 and are applied locally between the sheath and the valve/receptacle without having to be transmitted around lateral bends of the catheter. Sheath 1104 may have a profile from 18 to 36 Fr, typically being 20 to 29 Fr, and inflation fluid pressures may be up to 10, 20, or even 30 atm or more.

Referring now to FIGS. 8B, 8C, 9B, 9C, and 10B, optional recapture balloon 1118 can be used to move sheath 1104 back over partially deployed valve 1106 by transmitting inflation fluid along recapture fluid path 1136 so as to inflate and axially elongate recapture balloon 1118. Inflation of recapture balloon initially again drives distal end 1110 distally away from the receptacle and valve 1106. A tension member, here in the form of 3 axial straps that limit separation of distal flange 1126 from proximal flange 1122 and are initially stowed in nosecone 1142, limit elongation of the deployment system distal of the valve as shown. As can be understood with reference to FIGS. 8C, 8D, 9C, and 9D, further inflation of recapture balloon 1118 thus drives intermediate flange 1120 (and sheath 1104) proximally (with the inflation fluid in deployment balloon 1116 typically being allowed to flow proximally via the deployment fluid path to facilitate sheath movement over valve 1106). Recapture sheath movement forces are again generated and applied locally, here via the tension members, as generally described above. Such recapture may be desired, for example, to allow removal of the valve if the system user determines that an alternative valve or other therapy may be better suited for the patient, or to allow the valve to be moved to a new position relative to the tissues of the heart. Note that some deployment systems may obviate recapture balloon 1118, for example, by including a simple tension member (such as a shaft, one or more filament such as a suture, or the like) extending between distal end 1110 and proximal end 1108 of the catheter system, allowing the user to manually pull sheath 1114 over valve 1106; or when the valve is released by proximal retraction of the sheath by providing an outer full-length sheath that can be pushed distally over the catheter body and retracted sheath from outside the body, or by simply eliminating the recapture capability.

Referring now to FIGS. 8D, 8E, 9D, 9E, and 10B, after recapture of valve 1106 under sheath 1104 is complete, recapture balloon 1118 may be in an elongate inflated state and may have axially compressed deployment balloon 1116 to a shortened deflated state. The distal portion of the catheter (including the receptacle and the valve supported therein) may be moved so as to reposition the valve and better align the valve with the heart tissue for deployment, movement of the valve often being induced using an articulation system of the catheter disposed proximally of the receptacle. Once the valve is in the target position, deployment balloon 1116 can be inflated, inflation optionally being initiated with the recapture balloon in a partially inflated state. Inflation fluid can be allowed to pass along the deflation flow path, so that the recapture balloon can be deflated. If partial inflation of the deployment balloon 1116 indicates alignment remains good (see FIGS. 8E, 9E), deployment balloon 1116 can be continued until sheath 1104 is moved axially sufficiently to fully release valve 1106 from the receptacle of the deployment system (see FIGS. 8F, 9F). Once the self-expanding annular frame structure of valve 1106 has fully expanded into fixed engagement with the surrounding heart tissue, deployment balloon 1116 can optionally be deflated (see FIGS. 8F, 8G, 9F, 9G) and the distal deployment and recapture balloons can be withdrawn proximally through the frame of expanded valve 1106 (see FIGS. 8G, 9G) and past the prosthetic valve leaflets (not shown).

A variety of different fluid control systems may be coupled to proximal end 1108 of deployment system 1100 to control inflation of the deployment and recapture balloons. Optionally, fluid at controlled pressures and/or volumes may be transmitted along the deployment and recapture flow paths from a computer-controlled manifold, with the fluid flows optionally being controlled using solenoid valves, the valves regulating flow pressurized using a gas/liquid canister as described above. When the deployment and/or recapture balloons are to be included in a deployment system having an articulated portion using selective inflation of a subset of balloons to control a bending state (as will often be the case), the deployment and recapture fluid flow paths may make use of the multi-channel substrates and extrusions described above, or may be formed using different catheter features. Referring again to FIGS. 8A-8G, 39A-39G, and 40D, an exemplary hydro-mechanical balloon drive system 1102 includes a deployment drive balloon 1150 and a recapture drive balloon 1152, with the exemplary drive balloons having structures and functionality that largely mirrors that of deployment balloon 1116 and recapture balloon 1118 described above, but inducing the fluid flow and corresponding axial movement of the intermediate and inner shafts. More specifically, deployment drive balloon 1150 and recapture drive balloon 1152 are separated by an intermediate drive flange 1154 affixed to intermediate shaft 1130. A proximal drive flange 1156 forms the proximal end of recapture drive balloon 1152, and is affixed to inner shaft 1132, and a distal drive flange 1158 affixed to catheter shaft 1124 (and hence to the valve receptacle). Deployment drive balloon is in fluid communication with the deployment fluid path 1136 (and hence with the distal deployment balloon 1116), and recapture drive balloon 1152 is in fluid communication with the annular recapture fluid path 1134 (and hence with the distal recapture balloon 1118). As shown schematically in FIG. 9B, a drive handle 1160 (or other mechanical or electromechanical actuating mechanism) is coupled to proximal balloon drive system 1102, with a support 1162 axially coupled to distal drive flange 1158 and first and second axially moveable arms 1164, 1166 coupled to the intermediate and proximal drive flanges 1154, 1156 so as to induce independent axial compression of the drive balloons. A wide variety of mechanisms may be included in drive handle 1160 to provide axial movement of the drive flanges, including levers, gears, or the like.

Referring once again to FIGS. 8A, 8B, 9A, 9B, and 10D, actuating proximal handle 1160 so as to move intermediate drive flange 1154 distally can axially compress drive deployment balloon 1150, sending inflation fluid through the deployment fluid path 1136 to deployment balloon 1116. The deployment balloon cross-sections can correspond so that the movement distances are similar (or they can differ so as to enhance mechanical advantage or limit handle stroke in some embodiments). The proximal end of intermediate shaft 1130 moves axially with intermediate drive flange 1154, limiting shaft friction loads associated with the distal balloon and flange movement, and fluid flow path can be sealed so that the volumetric flow and pressure of the inflation fluid corresponds at the proximal end to the deployment movement at the distal end, providing visual and haptic feedback to the user regarding sheath movement. Proximal flange 1156 optionally moves with the intermediate flange.

The other sheath deployment and recapture movements described above are similarly mirrored at the proximal balloon drive system 1102. For example, referring now to FIGS. 8B-38D, 39B-39D, and 40B, movement of proximal drive flange distally toward intermediate drive flange 1154 can pressurize fluid in recapture drive balloon 1152, driving fluid along the recapture fluid path to the distal recapture balloon and inducing movement of the sheath 1104 proximally back over a partially deployed valve 1106 (with the deployment drive balloon 1150 expanding to accommodate fluid from the axially compressed distal deployment balloon 1116 to complete recapture). As can be understood with reference to FIGS. 8E, 8F, 9E, 9F, and 10B, re-deployment (or complete deployment of) prosthetic valve 1104 can be induced by completing axial compression of the deployment balloon to a deflated state. Elongation of both drive balloons can optionally shorten the distal balloon system if that will facilitate proximal withdrawal of the deployment system from the deployed prosthetic valve and/or vasculature.

Referring now to FIGS. 11A-11D, an alternative distal fluid driven sheath actuation system 1170 includes many of the components of deployment system 1100, with the fluid driving the sheath deployment and retraction being radially contained between inner and outer balloons. More specifically, in fluid-driven deployment system 1170, an intermediate catheter shaft 1172 extends distally along a catheter axis to an intermediate flange 1174. Intermediate shaft 1172 has a deployment fluid lumen 1176 and a separate recapture fluid lumen 1178, with the lumens being in fluid communication with a deployment port 1180 and a recapture port 1182 in intermediate flange 1174, the intermediate flange and intermediate shaft again being axially coupled to sheath 1104 (and hence moving axially relative to the valve and receptacle during sheath deployment and recapture). Fluid flowing distally along deployment fluid path 1176 flows to a space that is at least in part disposed between an outer deployment balloon wall 1184 and an inner deployment balloon wall 1186, with both balloons being folded with laterally opposed indentations so as to facilitate axial expansion and contraction. Fluid from recapture fluid path 1178 flows to a space between an outer recapture balloon wall 1188 and an inner recapture balloon wall 1190.

Figure 12:
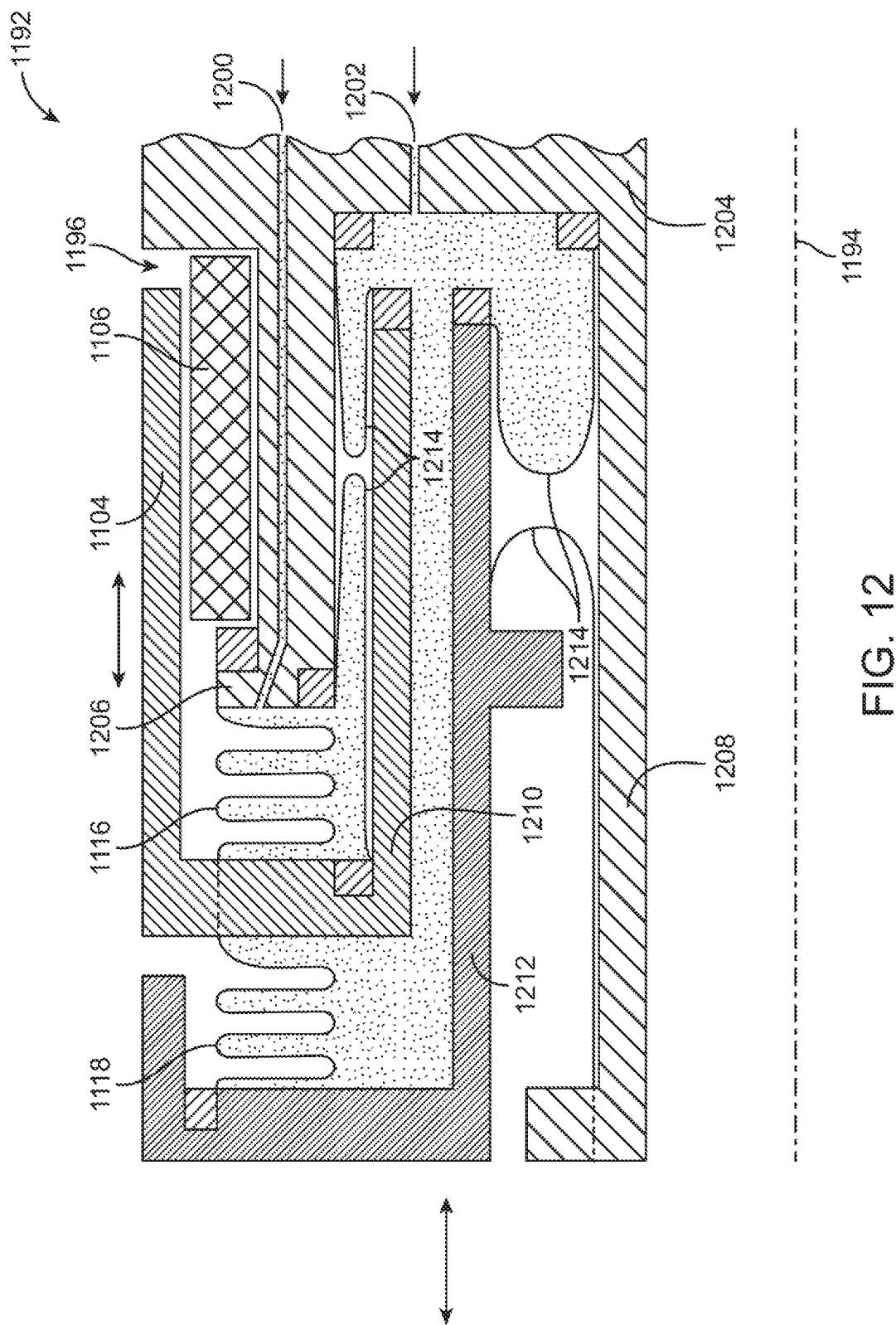
FIG. 12 is a schematic cross-section of another alternative valve delivery system having a fluid-driven sheath, wherein everting tubular membranes help seal the flowpath between distal shaft segments that move relative to, and distally of, a tool receptacle of an articulated catheter body.

Referring now to FIG. 12, a schematic illustration of yet another distal fluid driven sheath actuation system 1192 shows a cross section taken through one side of the distal catheter structure, with much of the remaining structure being symmetric about an axis 1194. This system avoids any need for axial movement of inner shafts along the body of the catheter significantly proximal of the valve receptacle 1196. Fluid flows to axially expand deployment balloon 1116 and recapture balloon 1118 through deployment fluid and recapture fluid lumens 1200 and 1202, respectively, in catheter shaft 1204. Catheter shaft 1204 has an outer distal tubular extension 1206 (on which a portion of the receptacle and proximal flange are formed) and an inner tubular extension 1208, defining an annular space in which an intermediate shaft segment 1210 and an inner shaft segment 1212 can move axially. Engagement of stops on the inner extension 1208 of the catheter body and the inner shaft limit distal travel of the inner shaft, so the inner extension and inner shaft work together as tension members to limit distal movement of the distal end of the catheter during inflation of deployment and recapture balloons 1116, 1118. Inflation fluid between the deployment lumens 1200 and the deployment balloon 1116 is sealed by evertable tubular membranes 1214. The tubular membranes can extend axially in the annular spaces between the extensions of the catheter body and the axially movable shaft segments, with everted ends oriented so as that the inflation fluid loads the membranes in tension, and so that both the inner and outer surfaces of the membrane are supported by adjacent surfaces bordering the annular spaces, and so that rolling eversion of the membrane accommodates axial movement of the shaft segments without sliding of the membrane against the bordering surfaces. Suitable evertable membrane materials may comprise semi compliant or compliant balloon materials as generally described herein. The membranes can be affixed to the catheter shaft and shaft segments using rings that snap into position and are held by detents of the shaft structures, by adhesive bonding, or the like.

Figure 13A:
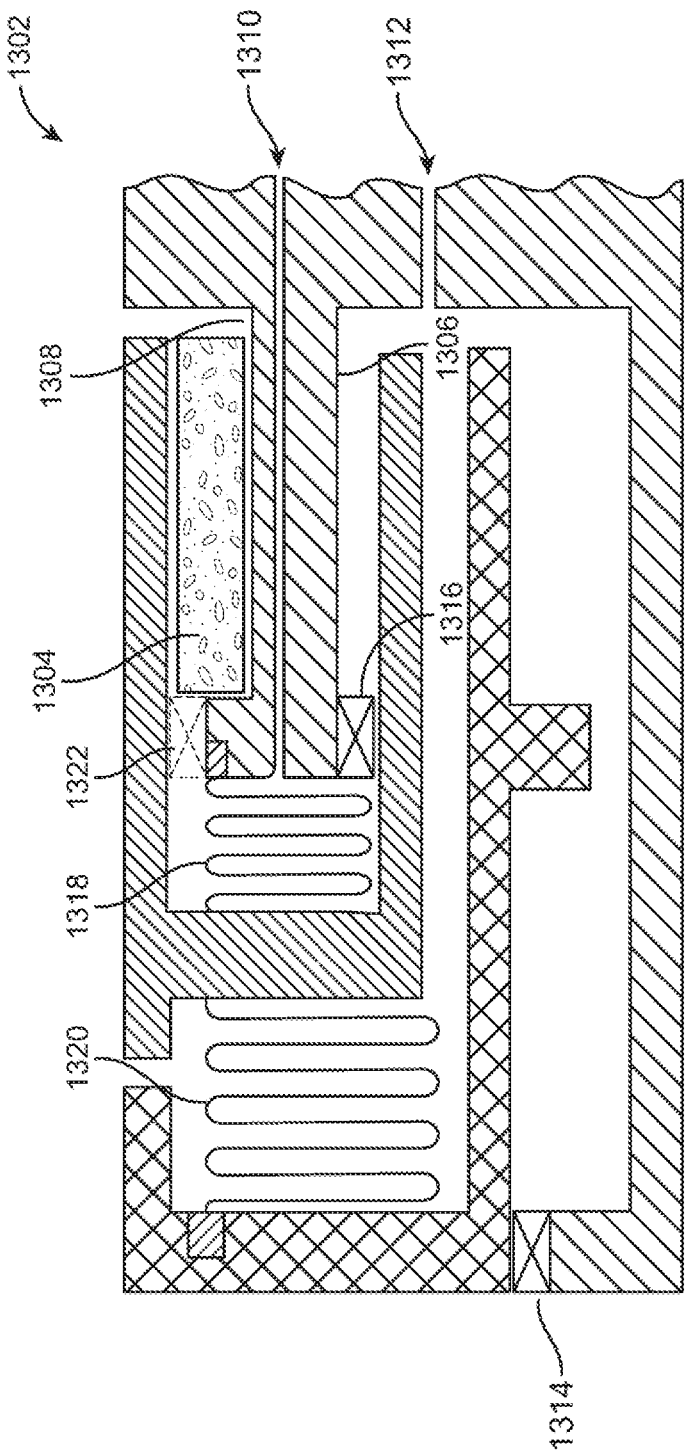
FIGS. 13A and 13B are a schematic cross-section and a schematic detail of another alternative valve delivery system having a fluid-driven sheath, wherein sliding tubular seals help maintain the inflation fluid flowpath between telescoping shaft segments that move relative to a tool receptacle, and in which an axial articulation balloon has an inflated outer diameter larger than an outer diameter of the sheath so as to provide desired axial articulation forces with moderate balloon inflation pressures.
Figure 13B:
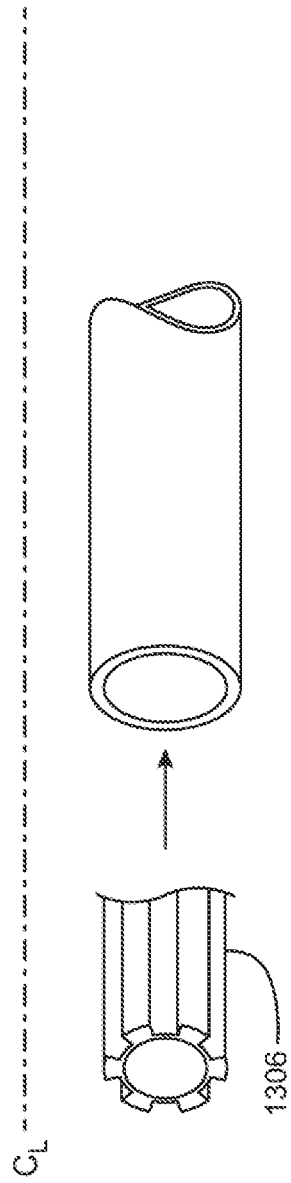

Referring now to FIGS. 13A and 13B, an alternative telescoping fluid driven sheath actuation system 1302 includes many components similar to those described immediately above, including a catheter having a receptacle configured for a prosthetic valve 1304. The receptacle is again mounted on an axial extension of the catheter body, with the extension here including an inner extension tube 1306 and an outer extension tube 1308. The inner and outer extension tubes 1306, 1308 can be bonded together, with either the inner surface of the outer extension or the outer surface of the inner extension or both having a circumferential series of channels, and the channels between the extension tubes can be used to form a portion of the deployment inflation fluid flow path 1310. While recapture fluid flow path 1312 is here shown schematically as being annular, there may be advantages to having the flow path instead being formed as a circumferential series of channels formed in one or both of the adjacent cylindrical surfaces. Moreover, rather than everting membranes for sealing of the flow paths round the axially slidable shafts, telescoping actuation system 1302 includes sliding seals 1314 to independently maintain pressure in deployment balloon 1318 and recapture balloon 1320. Recapture balloon 1320 may have an inflated cross-sectional profile or outer diameter that is significantly larger than a profile or outer diameter of sheath. This can facilitate application of significant axial prosthesis recapture loads against the sheath using moderate balloon inflation pressures (such as 20 atm or less, optionally being 26 or 30 atm or less) and commercially available balloons and balloon materials (such as nylon, PET, and ultra non-compliant balloons available from Bard). Optionally, another sliding seal 1322 between the catheter body extension and the inner surface of the sheath can be used in place of deployment balloon 1318, with the sliding seals 1316, 1322 bordering the chamber containing the balloon forming a sealed piston arrangement. Note that the opposed deployment and recapture actuators (balloons or pistons) may be used together to provide controlled axial positioning of the sheath relative to the receptacle. For example, by inflating the recapture balloon before beginning deployment of the valve, if the partially-expanded valve begins to push the sheath off, gradual and controlled draining of the recapture balloon can prevent the prosthetic valve from springing open more quickly than is desired.

Referring now to FIGS. 14A-14C, additional details of the large diameter recapture balloon 1320 can be understood. As seen in the exploded view of FIG. 14A, along with a balloon wall 1404, a proximal or distal end 1402 of balloon 1320 has a circumferential series of reinforcing struts 1406 that extend along the tapered end surface. Struts 1406 may comprise a metal such as stainless, a high-strength polymer, or the like, and can inhibit everting of the end of the balloon when the balloon is under a high axial load. Struts 1406 may be affixed to the tapered end surface of the balloon wall using a tapered polymer end cap 1408. Cap 1408 may comprise a balloon material (optionally being a material similar to that used to form the balloon wall), and the struts may be bonded and/or captured between the cap and the balloon wall material. As can be understood by comparison of the end of balloon 1320 in an inflated configuration (as shown FIG. 14B) to the illustration of the end of balloon 1320 in a small-profile configuration suitable for insertion into the patient (as shown in FIG. 14C), struts 1406 will generally move with the balloon as the balloon expands or contracts, with the balloon wall and cap between the struts folding to accommodate radial compression.

Figure 15A:
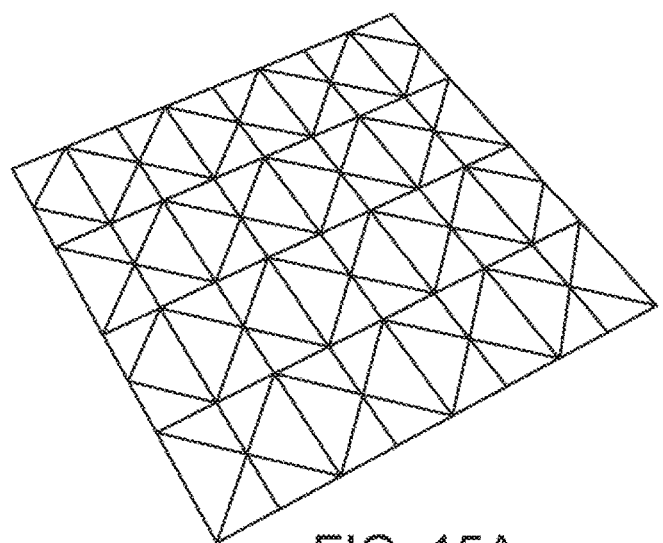
FIGS. 15A-15D illustrate origami balloon folding or buckling patterns that can accommodate inflation-induced changes to both axial length and cross-sectional profile.
Figure 15B:
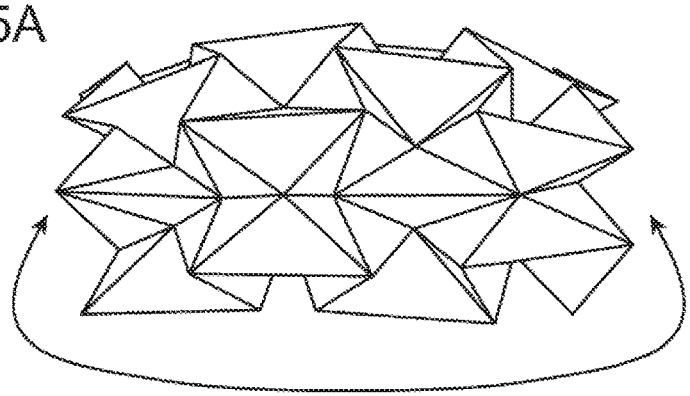
Figure 15C:
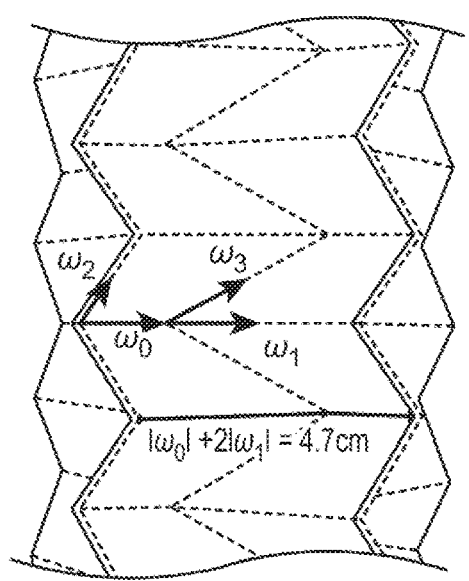
Figure 15D:
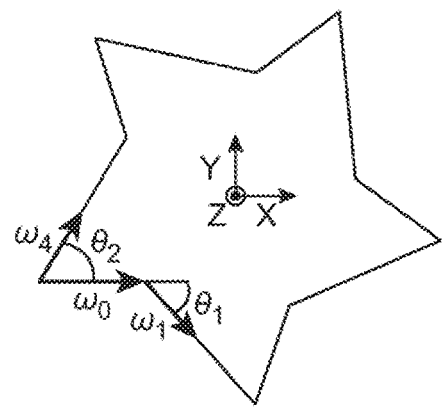

Balloon 1320 may benefit from a fold or buckle pattern 1410 that accommodates both radial and axial compression. Suitable patterns 1410 that may be imposed on the balloon may be identified or derived from the origami tessellation patterns that have been analyzed. Note that tooling to impose such fold patterns at specific locations might be provided, or simpler tooling can be used having shapes that promote desired origami-like buckling may be utilized. Suitable axially and radially compressible tubular fold or buckling patterns may include those sometimes described as magic ball or waterbomb patterns, herringbone patterns, Miura-Ori or other origami bellows patterns, or the like. Referring to FIGS. 15A and 15B, known computer software may be used to draw a desired fold pattern, such as a waterbomb fold pattern, with the lateral pattern edges being affixed together to form a generally cylindrical section of balloon 1320 so that outwardly oriented creases of the pattern extend radially so as to provide greater axial compression ratios. Suitable software may be available under the trade names ORIPA and FreeForm Origami, as described at their respective company website(s). The pattern can be adjusted at the ends of the balloon to accommodate struts 1406 and the tapered shape of the balloon end, and balloon performance can be analyzed using known modeling tools. Alternatively, a desirable balloon wall buckling pattern may be more generally imposed by providing a corresponding outer tubular tool and an inner tool to form a generally annular space, and compressing the balloon in that annular space. As can be understood with reference to FIGS. 15C and 15D, suitable tool cross-sections may have non-round shapes, and the annular space may taper radially along the annular axis to generate buckling patterns that accommodate radial and axial compression. A number of suitable fold or buckle patterns may be understood with reference to an article entitled "Geometry and Design of Origami Bellows with Tunable Response" by Austin Reid et al., dated Sep. 6, 2016.

Referring now to FIGS. 16A-16H-2 an alternative fluid actuated prosthetic mitral valve deployment and retrieval system 1602 related to that of FIGS. 8A-11D is shown. As generally described above, system 1602 includes an elongate flexible catheter body (see, e.g., FIG. 1-1) having a proximal end 1604 and a distal portion 1606 with an axis 1608 therebetween. A receptacle 1610 for receiving a therapeutic or diagnostic tool 1612 is along the distal portion of the catheter body, and a tubular sheath 1614 has a lumen 1616 slidably receiving the distal portion of the catheter therein. A first fluid channel 1618 and a second fluid channel 1620 extend axially along the catheter body. A first actuator 1622, preferably in the form of a deployment balloon, is disposed along the distal portion 1606 in fluid communication with the first channel 1618. The first actuator couples the distal portion 1606 with the sheath 1614 so that, in response to fluid transmitted along the first channel 1618, the first actuator drives the sheath axially between a first position 1624 over the receptacle and a second position 1626 axially offset from the first position such that the tool 1612 is uncovered for use. A second actuator 1628, preferably in the form of a recapture balloon, is in fluid communication with the second channel 1620, and the second actuator axially couples the distal portion of the catheter with the sheath 1614 so that transmission of inflation fluid along the second channel drives the sheath axially in opposition to the first actuator, and so as to extend a distal end 1630 of the catheter body distally relative to the receptacle 1610.

Sheath 1614 has an outer profile 1632. Advantageously, the second actuator 1628 can be inflatable from an insertion profile 1634 (similar to or less than the sheath profile) to an inflated profile 1636 larger than the sheath profile. The recapture balloon having an inflated profile that is larger than that of the sheath used to radially constrain the valve during insertion and positioning, along with methods for using the opposed balloons of the system to controllably deploy and recapture catheter-supported tools, can provide significant advantages for controlled delivery. As can be understood with reference to FIGS. 16A, 16B, and 16E-1-16F-3, once the distal portion of the catheter body has been advanced (and optionally articulated using a balloon array, pullwires, or the like) so that the prosthetic valve is in a desired position and orientation within the native valve tissue, the large-diameter recapture balloon may be inflated. Reinforcing struts 1638 along the balloon ends of the relatively large diameter recapture balloon may deflect outward with the adjacent balloon wall, with the struts here extending axially from an annular support along an outer surface of the balloon wall. Alternatively, the struts and ring may be disposed inside (and optionally bonded to an inner surface of) the balloon wall, as described above. In some embodiments, an elastomeric sheathing may extend over the recapture balloon and struts, with the sheathing providing radial compression forces to facilitate controlled reduction of the balloon diameter during deflation for removal and presenting a smooth, low-surface atraumatic outer surface to inhibit entanglement with cordae or other ventricular structures.

One or both of first and second actuators 1622 and 1628 may comprise a balloon. Such a balloon will typically have an uninflated configuration with an uninflated axial length, and the balloon(s) in the inflated configuration can have an inflated axial length greater than the uninflated axial length. In system 1602, the second balloon can be distal of the first balloon and the first balloon can be distal of the receptacle 1610. Preferably, a tension member 1640 extends axially along the first and second actuators 1622, 1628. The tension member can accommodate elongation of the second actuator prior to movement of sheath 1614 from over the tool 1612, but can limit the total combined length of the two actuators (similar to the tension member structures described above). Hence, after distal elongation of the end of the catheter during inflation of the second balloon 1628, transmission of the inflation fluid distally along the first channel 1618 can not only inflate the first actuator and urge the sheath from over the tool, but can also drive the inflation fluid from the second actuator 1628 proximally along the second channel 1620. This allows precise control of the movement of the sheath. Similarly, transmission of the inflation fluid distally along the second channel 1620 can drive the inflation fluid from the first actuator 1622 proximally along the first channel 1618.

Optionally, the tension member 1640 elongates axially from a first tension member configuration (shown in FIG. 16E-2) to a second, longer tension member configuration (shown in FIG. 16F-2) in response to transmission of the inflation fluid, and the tension member may inhibit elongation beyond the second tension member configuration so as to facilitate driving the sheath 1614 back over the receptacle 1610 by inflation of the second actuator or recapture balloon 1628. The tension member 1640 may comprise an inner tubular shaft 1642 and an outer tubular shaft 1644 slidingly receiving the inner shaft therein, with a stop inhibiting telescoping elongation of the shafts beyond the second tension member configuration. The shafts may comprise metal or a rigid polymer, optionally comprising stainless steel. Optionally, the first channel is disposed between the outer tubular shaft and an intermediate tubular shaft, the outer shaft is axially affixed to the tool receptacle, and the second channel is disposed between the inner shaft and the intermediate shaft.

Referring now to FIGS. 16B-16D and FIGS. 16F-1-16H-2, inflation of the deployment balloon can urge the sheath distally from over the compressed prosthetic valve, allowing the valve to expand into engagement with the native tissue. As the valve resiliently expands, it may urge the sheath distally with sufficient force to move the sheath without deployment force being imposed by the deployment balloon. As the recapture balloon is mounted in opposition to the deployment balloon with the tension member (here including a shaft assembly extending within the two balloons) limiting a combined axial length of the balloons, gradual deflation of the recapture balloon can be used to limit and control sheath movement in the distal deployment orientation. Releasable constraint members such as sutures or rigid features extending radially from the receptacle towards the sheath may pass through a frame of the prosthetic valve to inhibit axial movement of the valve relative to the receptacle until deployment is complete. If it is determined prior to complete deployment that it would be desirable to recapture and reposition or remove the prosthetic valve, inflation of the deployment balloon and deflation of the recapture balloon can be halted. Recapture can then be performed by inflating the recapture balloon and deflating the opposed deployment balloon. The large cross-sectional profile of the partially inflated recapture balloon allows relatively modest balloon inflation pressures (such as 20 atm or less, 26 atm or less, or 30 atm or less) to impose significant recapture forces. Once the prosthetic valve is fully expanded (optionally after recapture and repositioning), the balloons can be deflated, with the large recapture balloon optionally being radially contracted by a surrounding elastomeric sheath, by axially constraining the shaft assembly adjacent the balloons using sliding seals or a shaft inserted into the central guidewire lumen, or the like. The distal end of the catheter and the deflated balloon assembly can be withdrawn proximally through the expanded valve and out of the patient.

Referring now to FIGS. 17A-17H-2, a related alternative large-balloon mitral valve deployment and retrieval system structure is shown, along with a method for its use. The deployment can here be performed by positioning the prosthetic valve proximally of the target location relative to the native tissue using an articulation balloon array, a pullwire system, or the like. Using many of the components described above regarding FIGS. 16A-16H-2, but with the recapture balloon disposed proximally of the sheath and tool, the recapture balloon is again inflated prior to deployment. The deployment balloon can then withdraw the sheath proximally, so that the opposed balloon system can be used to axially advance and position the prosthetic valve relative to the native valve tissue prior to deployment. The opposed deployment and recapture balloons are here disposed proximally of the receptacle and prosthetic valve, and inflation of the recapture balloon can advance the prosthetic valve distally within the native valve tissue toward a target position. Articulation of the catheter proximal of the deployment balloons and receptacle can optionally be used to correct or fine-tune the deployment position and orientation of the axially advanced valve, and deployment may be initiated by inflation of the deployment balloon. A maximum combined length of the opposed deployment and recapture balloons is again constrained by a tension member (defined at least in part by a shaft assembly extending axially within the balloons), so that gradual deflation of the recapture balloon can provide controlled prosthetic valve expansion despite relatively high radial and axial resilient forces imposed by the valve against the sheath. Deployment may be halted and the valve recapture by inflation of the recapture balloon and gradual deflation of the deployment balloon.

While the exemplary embodiment have been described in some detail for clarity of understanding and by way of example, a variety of modifications, changes, and adaptations of the structures and methods described herein will be obvious to those of skill in the art. Hence, the scope of the present invention is limited solely by the claims attached hereto.

What is claimed is:

1. A catheter-based tool deployment system comprising:
   an elongate flexible catheter body having a proximal end and a distal portion with an axis therebetween;
   a receptacle for receiving a therapeutic or diagnostic tool along the distal portion of the catheter body;
   a tubular sheath having a lumen slidably receiving the distal portion of the catheter body therein, wherein the tubular sheath has an outer cross-sectional profile;
   a first fluid channel and a second fluid channel extending axially along the catheter body;
   a first actuator disposed along the distal portion in fluid communication with the first channel, the first actuator coupling the distal portion with the sheath so that, in response to fluid transmitted along the first channel, the first actuator drives the sheath axially between a first position over the receptacle and a second position axially offset from the first position such that the tool is uncovered for use; and
   a second actuator in fluid communication with the second channel, wherein the second actuator axially couples the distal portion of the catheter body with the sheath so that transmission of inflation fluid along the second channel drives the sheath axially in opposition to the first actuator and extends a distal end of the catheter body distally relative to the receptacle;
   wherein the second actuator comprises a balloon expandable from an uninflated configuration having an uninflated cross-sectional profile to an inflated configuration having an inflated cross-sectional profile in response to the transmission of inflation fluid along the second channel, wherein the inflated cross-sectional profile is larger than the sheath profile.

2. The system of claim 1, wherein the balloon in the uninflated configuration has an uninflated axial length, the balloon in the inflated configuration has an inflated axial length greater than the uninflated axial length, wherein the balloon axially couples the distal portion of the catheter body with the sheath so that transmission of inflation fluid along the second channel extends the distal end of the catheter body distally relative to the receptacle.

3. The system of claim 1, wherein the first actuator comprises a first balloon and wherein the balloon of the second actuator comprises a second balloon.

4. The system of claim 3, where the second balloon is distal of the first balloon and the first balloon is distal of the receptacle.

5. The system of claim 2, further comprising a tension member extending axially along the first and second actuators, the tension member limiting distal advancement of the distal end of the catheter body during inflation of the second balloon so that transmission of the inflation fluid distally along the first channel can drive the inflation fluid from the second actuator proximally along the second channel, and so that transmission of the inflation fluid distally along the second channel can drive the inflation fluid from the first actuator proximally along the first channel.

6. The system of claim 5, wherein the tension member elongates axially from a first tension member configuration to a second tension member configuration in response to transmission of the inflation fluid, the tension member inhibiting elongation beyond the second tension member configuration so as to facilitate driving the sheath back over the receptacle.

7. The system of claim 6, wherein the tension member comprises an inner tubular shaft and an outer tubular shaft slidingly receiving the inner shaft therein with a stop inhibiting telescoping elongation of the shafts beyond the second tension member configuration.

8. The system of claim 7, wherein the shafts comprise metal or a rigid polymer.

9. The system of claim 1, the tool comprising an endoluminal implant biased to expand from a small profile configuration to a large profile configuration, wherein the sheath is configured to radially constrain the implant in the first position and to slide axially over the implant from the first position toward the second position so as to radially release the implant.

10. The system of claim 1, wherein the tool comprises a prosthetic valve.

11. The system of claim 10, wherein the valve comprises a prosthetic mitral valve.

12. The system of claim 1, wherein the distal portion of the catheter body comprises an articulated segment disposed proximally of the receptacle.

13. The system of claim 12, wherein the articulated segment comprises an articulation balloon array.

14. The system of claim 12, wherein the distal portion of the catheter body comprises a plurality of articulated segments configured to position and orient a prosthetic valve with at least 3 degrees of freedom.

15. The system of claim 1, wherein the second position of the sheath is distal of the first position so that the sheath moves distally and away from bends of the catheter body disposed between the receptacle and the proximal end when uncovering the tool for use.

16. The system of claim 15, wherein the first channel is disposed between an outer tubular shaft and an intermediate tubular shaft, the outer shaft axially affixed to the receptacle, and wherein the second channel is disposed between an inner shaft and the intermediate shaft, a tension member axially coupling the inner shaft to the outer shaft.

17. The system of claim 1, further comprising a plurality of reinforcing struts extending radially along the proximal balloon end, the distal balloon end, or both so as to facilitate transmission of axial balloon actuation forces between the catheter body and the sheath.

18. A catheter-based tool deployment system comprising:
 an elongate flexible catheter body having a proximal end and a distal portion with an axis therebetween;
 a receptacle for receiving a therapeutic or diagnostic tool along the distal portion of the catheter body;
 a tubular sheath having a lumen slidably receiving the distal portion of the catheter body therein;
 a first fluid channel and a second fluid channel extending axially along the catheter body;
 a first actuator disposed along the distal portion in fluid communication with the first channel, the first actuator coupling the distal portion with the sheath so that, in response to fluid transmitted along the first channel, the first actuator drives the sheath axially between a first position over the receptacle and a second position axially offset from the first position such that the tool is uncovered for use; and
 a second actuator in fluid communication with the second channel, wherein the second actuator axially couples the distal portion of the catheter body with the sheath so that transmission of inflation fluid along the second channel drives the sheath axially in opposition to the first actuator and extends a distal end of the catheter body distally relative to the receptacle;
 wherein the first actuator comprises an axially segmented balloon having a balloon axis extending along the axis of the catheter body, a first end axially coupled with the receptacle and a second end axially coupled with the sheath so that inflation pressure against the first and second ends increases an axial length of the balloon and drives the sheath, wherein the segmented balloon has an outer wall with a plurality of radial members extending radially inwardly from the balloon wall toward a shaft of the catheter body extending axially within the balloon.

19. A catheter-based prosthetic heart valve deployment and recapture system comprising:
 an elongate flexible catheter body having a proximal end and a distal portion with an axis therebetween, the distal portion configured for supporting a prosthetic heart valve;
 a tubular sheath having a lumen slidably receiving the distal portion therein, the sheath having an outer diameter;
 a first fluid channel extending axially along the catheter body; and
 a recapture balloon in fluid communication with the first channel and axially coupling the distal portion of the catheter body with the sheath so that when inflation fluid is transmitted along the first channel the recapture balloon drives the sheath axially toward a first position disposed over the heart valve and away from a second position axially offset from the heart valve so that the heart valve is recaptured, the recapture balloon being inflated during recapture of the heart valve from an insertion diameter suitable for insertion of the heart valve to an inflated diameter, the inflated diameter being larger than the outer diameter of the sheath during recapture of the heart valve so as to enhance an axial recapture force applied by the recapture balloon to the sheath.

20. A method for recapturing a catheter-based heart valve, the method comprising:

introducing an elongate flexible catheter body distally into a patient body, the distal portion supporting the heart valve;

transmitting fluid distally from outside the patient into a first channel extending along the catheter body; and radially expanding a balloon and axially driving a tubular sheath, with the transmitted fluid, wherein the axial driving of the sheath is performed with an axial recapture force generated by the radially expanded balloon so the sheath moves over the distal portion, toward a first position over the heart valve and away from a second position axially offset from the heart valve, and wherein the sheath has an outer cross-sectional diameter, wherein the radial expanding of the balloon increases an outer diameter of the balloon from an insertion outer diameter suitable for insertion on the heart valve to an inflated outer diameter larger than the sheath when the balloon drives the sheath axially so as to enhance the axial recapture force.

* * * * *